United States Patent [19]
Ohtani et al.

[11] Patent Number: 5,811,682
[45] Date of Patent: Sep. 22, 1998

[54] ELECTROMAGNETIC ACOUSTIC TRANSDUCER EMAT AND INSPECTION SYSTEM WITH EMAR

[75] Inventors: Toshihiro Ohtani, Kanagawa-ken; Hirotsugu Ogi; Masahiko Hirao, both of Osaka, all of Japan

[73] Assignee: Ebara Corporation, Tokyo, Japan

[21] Appl. No.: 766,471

[22] Filed: Dec. 12, 1996

[30] Foreign Application Priority Data

Dec. 13, 1995 [JP] Japan .................................. 7-347206
Dec. 13, 1995 [JP] Japan .................................. 7-347207
Mar. 21, 1996 [JP] Japan .................................. 8-091901

[51] Int. Cl.⁶ .................................................. G01N 29/24
[52] U.S. Cl. .................................. 73/643; 73/622; 73/661
[58] Field of Search ........................... 73/643, 632, 661, 73/622

[56] References Cited

U.S. PATENT DOCUMENTS

| | | | |
|---|---|---|---|
| 4,434,663 | 3/1984 | Peterson et al. | 73/643 |
| 4,452,086 | 6/1984 | Hüschelrath et al. | 73/643 |
| 4,593,567 | 6/1986 | Isselstein et al. | 73/643 |
| 4,777,824 | 10/1988 | Alers et al. | |
| 5,503,020 | 4/1996 | Mandracchia | 73/643 |
| 5,608,164 | 3/1997 | MacLauchlan | 73/643 |
| 5,608,691 | 3/1997 | MacLaulan et al. | 73/643 |

FOREIGN PATENT DOCUMENTS

| | | |
|---|---|---|
| 0 458 425 | 11/1991 | European Pat. Off. . |
| 26 57 957 | 6/1978 | Germany . |
| 39 04 440 | 8/1990 | Germany . |
| 2 006 433 | 5/1979 | United Kingdom . |

*Primary Examiner*—Hezron E. Williams
*Assistant Examiner*—Nashmiya Fayyaz
*Attorney, Agent, or Firm*—Oblon, Spivak, McClelland, Maier & Neustadt, P.C.

[57] ABSTRACT

An electromagnetic acoustic transducer for magnets and a sheet type coil unit. The magnets are permanent magnets or electromagnets to provide a static magnetic field to an object to be inspected. The coil unit includes a pair of spiral or meander coils of an electrically conductive material, sandwiched between upper and middle insulation sheet and middle and lower insulation sheet. The coils are used for transmission and reception, respectively. All the ends of the respective coils extend through throughholes formed through the upper and middle insulation sheets to the surface of the ultrasonic transducer, and are connected to external leads. The ends for earth are commonly connected to form a common ground terminal. The inspection system with the electromagnetic acoustic resonance which is a combination of resonant technique and a non-contact electromagnetic acoustic transducer can evaluates the absolute value of ultrasonic attenuation. The attenuation is highly sensitive to the accumulated fatigue damage, showing a maximum around 20–30% of the whole life. This system can assess damage and predict the fatigue life of metals.

17 Claims, 22 Drawing Sheets

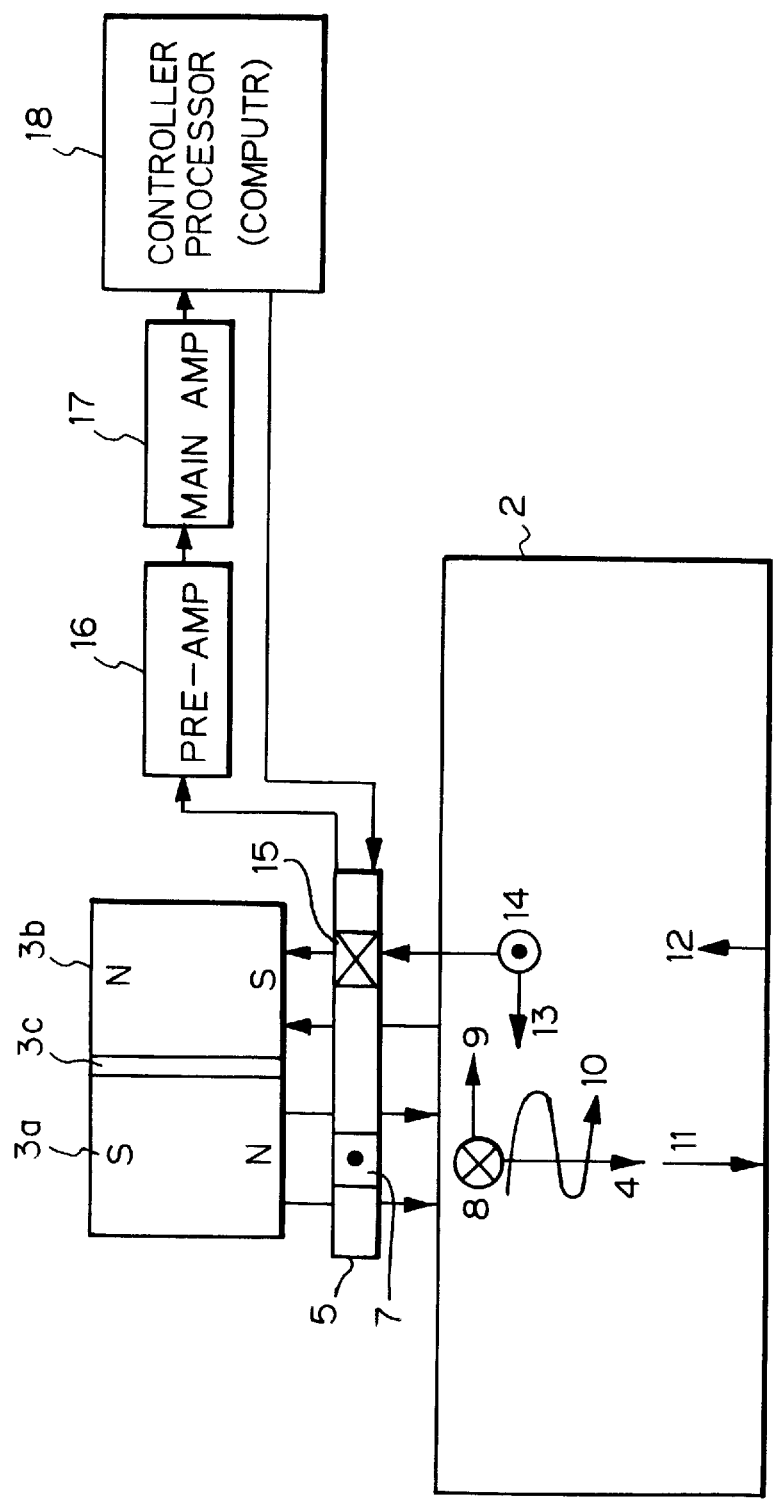

DURING TRANSMITTING

DURING RECEIVING

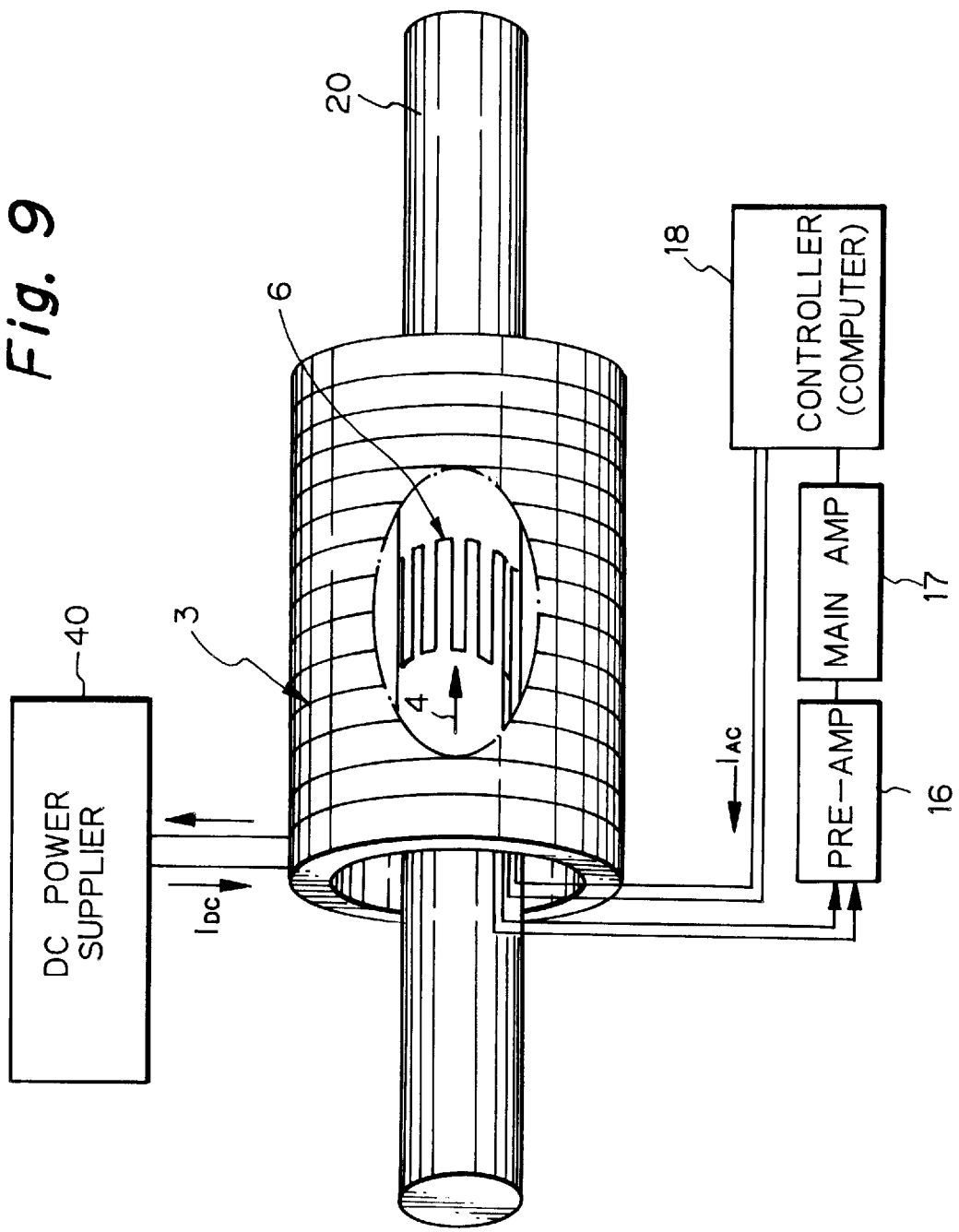

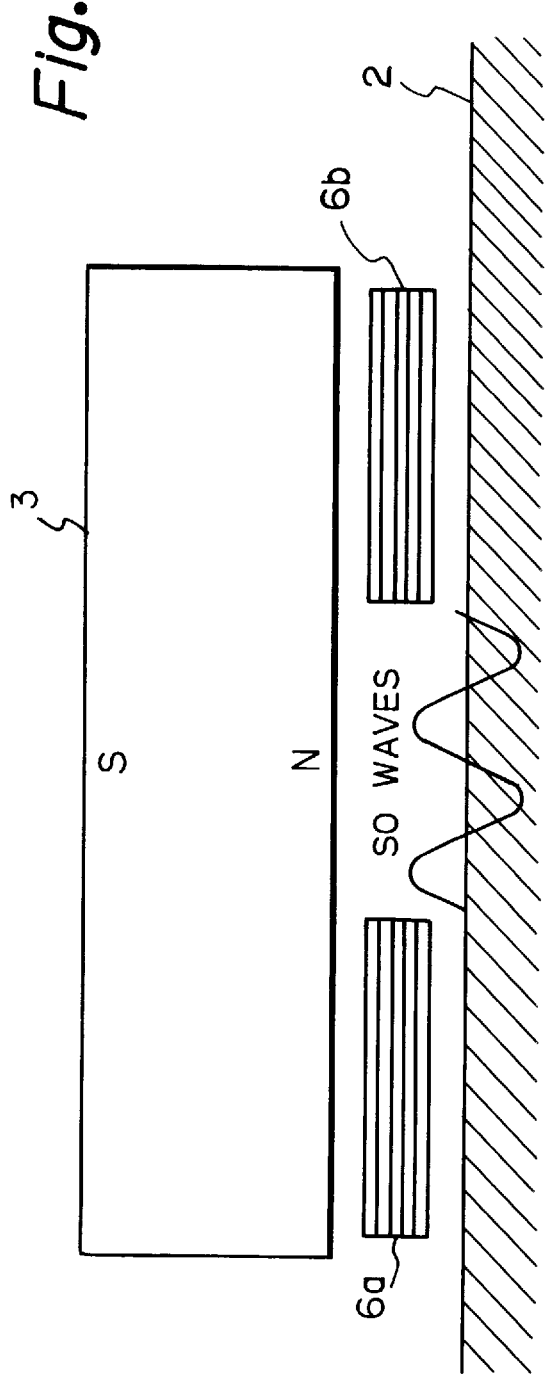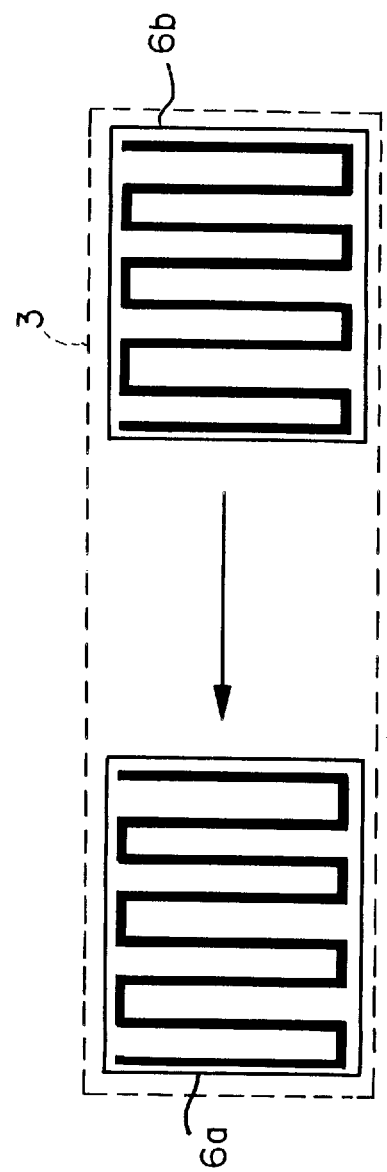

ELECTROMAGNETIC ACOUSTIC TRANSDUCER EMAT AND INSPECTION SYSTEM WITH EMAR

BACKGROUND OF THE INVENTION

The present invention relates generally to an electromagnetic acoustic transducer (EMAT) which is suitable for applications for detecting surface and internal damages and residual stress of an electrically conductive material, measuring the characteristics of the material (such as elastic modules, and attenuation coefficient), and detecting damages and deterioration in the interior of the material due to load, heat, and so on, and to an inspection system with the electromagnetic acoustic resonance which is a combination of resonant technique and non-contacting EMAT, and which improves fairly the signal to noise ration (S/N) and compensates for the weak coupling efficiency of the EMAT.

FIG. 1 is a diagram for explaining the measuring principles of an inspection system using an EMAT. The EMAT transducer consists of a pair of permanent magnets $3a$, $3b$ which have the opposite magnetization direction normal to the objects 2 surface, that is a conductive material, through a spacer $3c$, and an elongated electrically spiral elongated coil unit 5 positioned below the permanent magnets $3a$, $3b$. The permanent magnets may be replaced with electromagnets which can form a similar magnetic field.

The permanent magnets $3a$, $3b$ generate a static magnetic field 4 in the depth direction of the object 2. When the coil unit 5 is supplied with a rf burst current 7 from a controller or processor 18, an eddy current 8 is generated on the surface of the object 2 in the direction reverse to that of the current 7. Then, the eddy current 8 and the static magnetic field 4 interact to generate a Lorentz force 9 in accordance with the so-called Fleming's law. The Lorentz force 9 acts on internal free electrons of the object 2 to cause collision with ions and so on, to induce movements thereto in a direction perpendicular to the directions of the static magnetic field 4 and the rf burst current 7 in the interior of the object 2, and to generate ultrasonic shear waves 10.

As the ultrasonic shear waves 10 travel in a direction indicated by an arrow 11, the ultrasonic shear waves 10 reflect on the upper and lower surfaces of the object 2 and interior damages, defects, grain boundaries, changes of material's structure and so on therein, and thereby return in a direction indicated by an arrow 12. When the reflected ultrasonic shear waves 10 return to the vicinity of the upper surface, a force 13 is generated. Then, an eddy current 14 is generated by an interaction of the force 13 and the static magnetic field 4. The eddy current 14 is detected by the spiral elongated coil unit 5 and the detected current is amplified by a pre-amplifier 16 and a main amplifier 17, and then sent to the controller 18. The controller 18 analyzes the received current to measure internal damages, defects, grain boundaries, changes of material's structure and so on of the object 2.

FIGS. 2($a$) and 2($b$) schematically illustrate a conventional EMAT composed of a pair of permanent magnets $3a$, $3b$ and a spiral elongated coil unit 5, which is usable in an inspection system as shown in FIG. 1. FIG. 2($a$) is a top plan view of the transducer and FIG. 2($b$) is a cross-sectional view taken along a line A—A in FIG. 2($a$). The spiral elongated coil unit 5 includes a transmitter coil $51a$ and a receiver reception coil $51b$ which are fabricated by manually winding a pair of enamel wires closely to each other and by solidifying the wound enamel wires with a resin. The spiral elongated coil unit 5 further includes a protection film 52 having a thickness of approximately 0.1 mm adhered thereto to support and protect the coils $51a$, $51b$. By the protection film, when a ferromagnetic object to be inspected is placed, the spiral elongated coil unit 5 may be prevented from damages caused by magnetic forces generated by the permanent magnets $3a$, $3b$ and the ferromagnetic object. A space or spacer $3c$ is interposed between the permanent magnets $3a$, $3b$ which have the oppose magnetization directions.

The conventional EMAT shown in FIG. 2 requires the protection film 52 adhered on the surface of the spiral elongated coil unit 5 in order to prevent the unit 5 from being damaged. Also, since the receiver and transmitter coils $51a$, $51b$ are arranged on the same surface adjacent to each other, the spiral elongated coil unit 5 inevitably has a large flat size. Further, since the coils $51a$, $51b$ is made by manually winding enamel wires, dispersions in the winding of wires are caused, and thus resulting in wide variations in the performance of finished transducers. Accordingly, it may not provide a stable quality.

As to other conventional spiral elongated coil units for generation and detection of ultrasonic waves which EMAT, the following prior arts have been provided, for example: Japanese Patent Public Disclosure (Laid-Open) No. 53-1078 (1978) discloses a structure having double spiral coils arranged on the opposing sides of an insulation substrate for providing separate transmission and reception coils. However, although the structure has the separate transmission and reception coils, the two coils are not provided with a common ground, thus exhibiting a low S/N ratio and a small gain.

Japanese Patent Public Disclosure (Laid-Open) No. 62-277555 (1987) discloses a structure having a single parallel coil on one surface of an insulation substrate so as to use the coil for both transmission and reception. In this prior structure, since the single parallel coil arranged on one surface of the insulation substrate is used for both transmission and reception, the S/N ratio is low and the gain is small.

Japanese Patent Public Disclosure (Laid-Open) No. 53-23066 (1978) discloses parallel coils formed on one surface of an insulation substrate in an "8" shape (i.e., two coils winding in opposite directions) using printing techniques. In this prior art, since the 8-shaped parallel coil is formed on one surface of the insulation substrate, the entire size becomes larger. In addition thereto, since the two coils are not provided with a common ground, the S/N ratio is low and the gain is small.

FIG. 3 shows another conventional inspection system (excluding a controller and amplifier means) for detecting surface and internal damages and residual stress of an electrically conductive material, measuring the characteristics of the material (such as elastic modules, and attenuation coefficient), and detecting damages and deterioration in the interior of the material due to load, heat, and so on. In the system, an EMAT comprises a meander coil unit 6 positioned on an inspection object 2 of a flat steel plate, and a permanent magnet 3, which generates a static magnetic field or bias magnetic field, positioned above the meander coil unit 6.

When the meander coil unit 6 of the EMAT is applied with a rf burst current from a controller (not shown), rf burst currents flow on the surface of the object beneath parallel lines of the meander coil unit 6 in alternate directions. This results in generating Lorentz forces 9 in reverse directions to each other, which in turn generate ultrasonic waves 10 in the direction perpendicular to the parallel lines of the meander coil unit 6 on the object 2. When the ultrasonic waves (SO wave) 10 reflect on damages, defects, grain boundaries, structural changes, and so on on the surface and in the interior of the object 2, and reflect on the opposing surface of the object 2. When the reflected waves reach the vicinity of the surface of the object 2, a force is generated. Then, a current is generated by an interaction of this force and the static magnetic field, and detected by the meander coil unit 6 to measure damages, defects, grain boundaries, structural changes, and so on on the surface and in the interior of the object 2.

The conventional meander coil type EMAT shown in FIG. 3 uses a single coil in the coil unit both as a transmitter coil for generating ultrasonic waves and as a receiver coil having a detecting function. For this reason, the transducer exhibits a low S/N ratio and a small gain. In addition thereto, since the meander coil unit 6 is constituted to be flat and not to be flexible, the transducer cannot be utilized for a cylindrical object to measure damages, defects, grain boundaries, organizational changes, and so on on the surface and in the interior thereof.

In a prior art, a fatigue life and a remaining life of a metal material at an initial stage of its fatigue process is predicted by using a piezoelectric ultrasonic transducer, contacting ultrasonic transducer. As illustrated in FIG. 4(a), a piezoelectric ultrasonic transducer (P.Z.T) 21 vibrates to generate ultrasonic waves which mechanically propagate to an object 2 of a metallic material through a protective film 22 and an acoustic couplant 23 during transmitting. During receiving, the process reverse to the transmission is performed, as illustrated in FIG. 4(b), wherein vibrations of the object 2 mechanically propagate through the acoustic couplant 23 and the protective film 22 to the piezoelectric ultrasonic transducer 21 which transduces the mechanical vibrations into ultrasonic waves. The ultrasonic waves are processed and analyzed by a controller (not shown) to predict fatigue life and remaining life of the object 2.

In the above conventional method of predicting a fatigue life and a remaining life, the ultrasonic waves often scatter due to reflections on interfaces (those are an interface between the piezoelectric ultrasonic transducer 21 and the protective film 22, an interface between the protective film 22 and the acoustic couplant 23, and an interface between the acoustic couplant 23 and the object 2) during its propagation process. Due to the scattering or absorbing ultrasonic waves, energy, which would otherwise be received by the piezoelectric ultrasonic transducer 21, leaks, and a phase change of the waves occurs when they reflect, thus resulting in disturbed signals.

Also disadvantageously, the characteristic and thickness of the acoustic couplant 23 are likely to vary due to change of temperature and pressing force applied thereto, so that measured values may often widely vary. In addition, measured values also fairly vary unless a measuring surface of an object is finely finished. For these reasons, a relative comparison with an initial value before fatigue has been used in a fatigue life and remaining life prediction method relying on attenuation of ultrasonic waves detected by the piezoelectric ultrasonic transducer 21. Further, it is difficult to measure the absolute attenuation of the ultrasonic waves to predict the lifetime of the object.

A prior document states that in a measurement of attenuation characteristics during a fatigue developing process using a piezoelectric ultrasonic transducer, the attenuation increases linearly at first and rises rapidly at about 70–80% of fatigue life, and the attenuation abruptly shown in FIG. 5.

Thus, if remaining life is evaluated based on a point at which the attenuation abruptly increases, while monitoring the fatigue process, it is necessary to monitor the fatigue process up to a rather later time of the lifetime.

SUMMARY OF THE INVENTION

The present invention has been made in view of the problems of the prior arts as mentioned above, and it is a first object of the present invention to provide an EMAT which is capable of increasing the S/N ratio and the gain as well as achieving improved performance, stable quality, finer structure, and reduction in size.

A second object of the present invention is to provide a fatigue life prediction apparatus based on electromagnetic ultrasonic resonance (EMAR) which is capable of accurately capturing changes within an object under measurement during a fatigue developing process and evaluating remaining life at an earlier time in the fatigue progress, without disturbed signals due to interfaces during the propagation of ultrasonic waves, and without the necessity of finely finishing surfaces of the object.

In order to achieve the first object of the present invention, an EMAT of the present invention consists of: magnets means for providing a static magnetic field to an object to be inspected; and sheet type coil means for making said object to transmit and receive ultrasonic waves in said object, said coil means including a first insulation layer and a pair of coils which are made of an electrically conductive material, are formed on opposing surfaces of said first insulation layer, and are positioned to coincident with each other through said insulation layer.

In order to achieve the second object of the present invention, a fatigue life prediction system according to the present invention comprises: an electromagnetic acoustic transducer (EMAT); a controller for instructing said EMAT to generate a rf burst ultrasonic signal at a resonance cycle in an object to be inspected to cause an ultrasonic wave resonance, and to receive a reflected ultrasonic signal; and processing means for processing said received signal to derive an attenuation coefficient, and estimating a remaining lifetime of said object from a change in said attenuation coefficient.

BRIEF DESCRIPTION OF DRAWINGS

FIG. 1 is a diagram for explaining the measuring principles by an inspection system using an electromagnetic acoustic transducer;

FIG. 9 shows an inspection system using a meander coil type electromagnetic acoustic transducer;

FIGS. 12–17 schematically illustrate inspection systems using meander coil type electromagnetic acoustic transducers, respectively, according to the present invention;

DESCRIPTION OF THE PREFERRED EMBODIMENTS

Figure 2A:
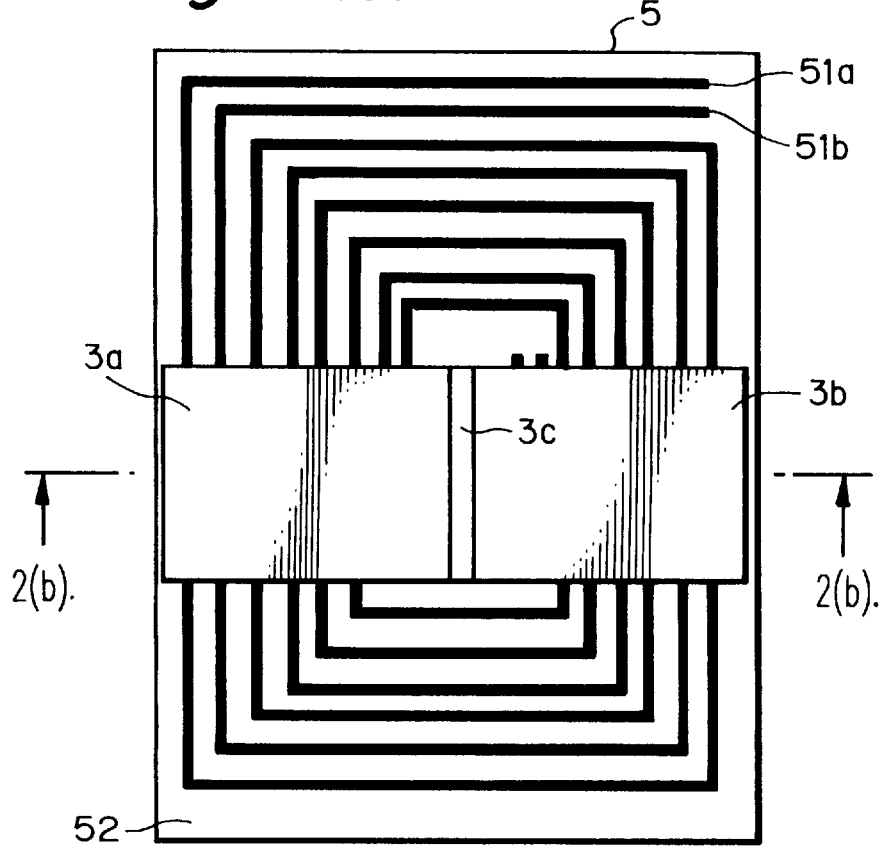
FIG. 2(a) is a top plan view schematically illustrating an electromagnetic acoustic transducer for polarized shear waves according to a prior art.
Figure 2B:
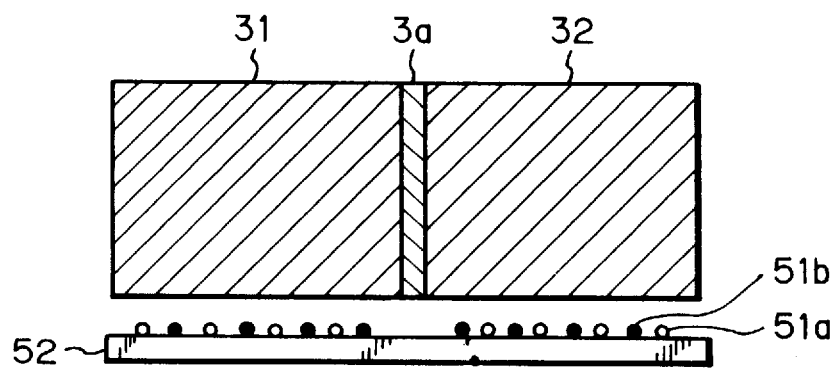
FIG. 2(b) is a cross-sectional view taken along a line A—A of FIG. 2(a)

Embodiments of the present invention will hereinafter be described with reference to FIGS. 6–22.

In these drawings, the same or similar components as or to those in FIGS. 1–5 are denoted with the same reference numerals as those in the latter.

Figure 6A:
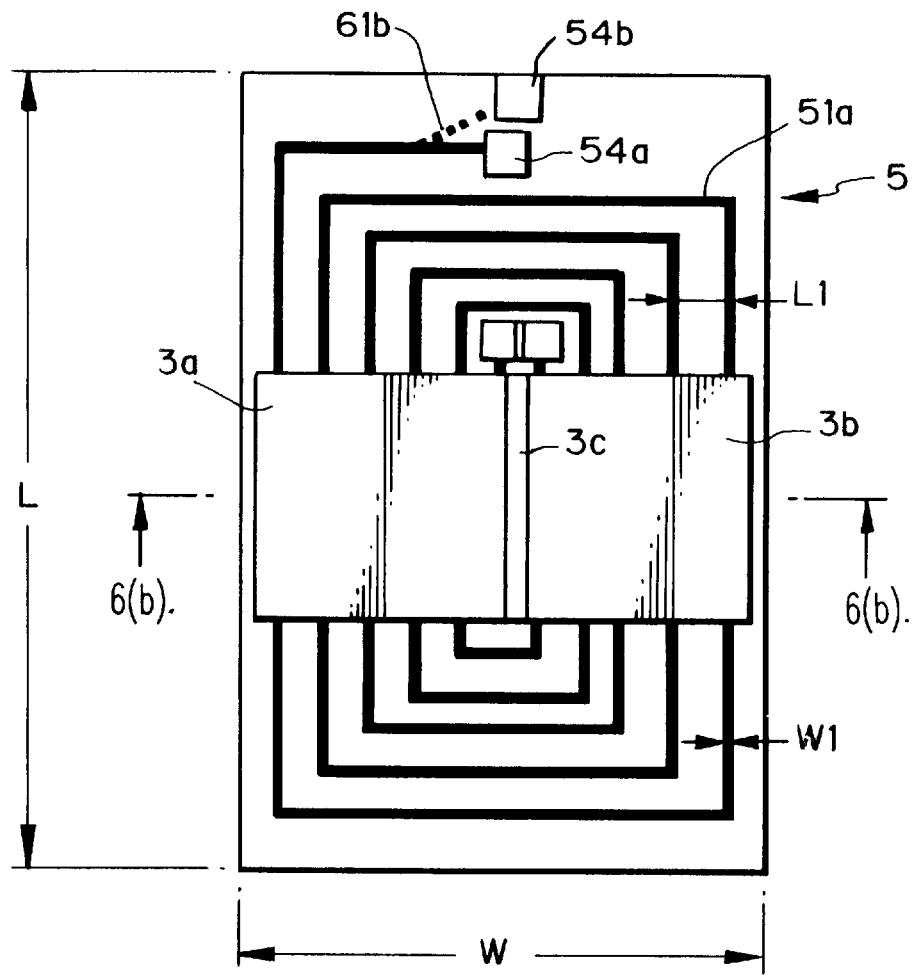
FIG. 6(a) is a top plan view schematically illustrating an electromagnetic acoustic transducer for deflected shear waves according to the present invention.
Figure 6B:
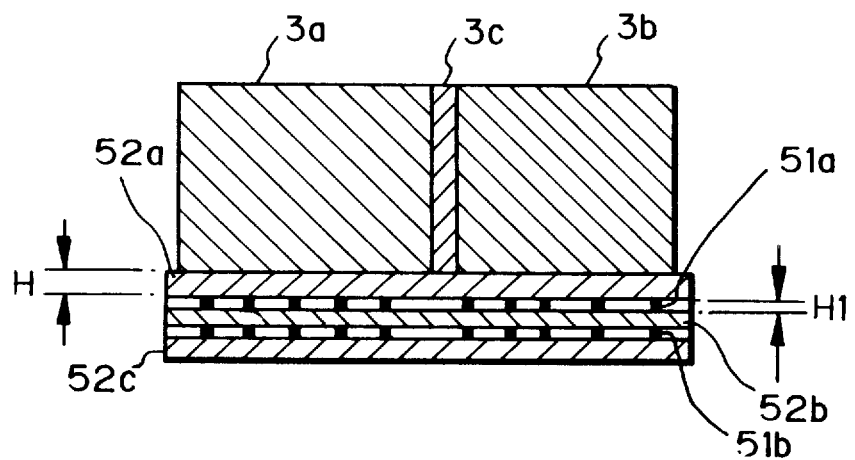
FIG. 6(b) is a cross-sectional view taken along a line A—A of FIG. 6(a)

FIGS. 6 and 7 show an embodiment of an electromagnetic acoustic transducer for polarized shear waves according to the present invention. FIG. 6(a) is a top plan view illustrating the transducer, provided that a top insulation sheet 52a of a flat spiral elongated coil unit 5 is neglected therefrom, and FIG. 6(b) is a cross-sectional view of the transducer, taken along a line A—A of FIG. 6(a). The illustrated electromagnetic acoustic transducer for polarized shear waves comprises a pair of permanent magnets (or electromagnets) 3a, 3b and a flat spiral elongated coil unit 5. The flat spiral elongated coil unit 5 comprises spiral coils 51a, 51b made of an electrically conductive material and respectively formed on upper and lower surfaces of a middle insulating sheet 52b, as shown in FIG. 6(b), using etching or printing techniques. The spiral elongated coils 51a, 51b are positioned opposite to and coincident with each other through the insulating sheet 52b. The flat spiral elongated coil unit 5 further comprises a lower insulating sheet 52c adhered on outer surface of the spiral coil 51b with a heat-resistant and insulating bonding adhesive. The top insulation sheet 52a is also adhered on the surface of the spiral coil 52a with a heat-resistant and insulating bonding adhesive. Therefore, the sheets 52a and 52b sandwich the spiral coil 51a while the sheets 52b and 52c sandwich the spiral coil 51b.

One of the spiral coils 51a, 51b serves as a transmitter coil for emitting electromagnetic ultrasonic waves, and the other one serves as a receiving coil having ultrasonic waves detecting function. While it is not necessary to determine which of the transmitter coil and the receiving coil is positioned above the other one, electromagnetic acoustic transducers generally have better receiving characteristics than transmission characteristics, so that the transmitter coil is often positioned closer to an object.

Figure 7A:
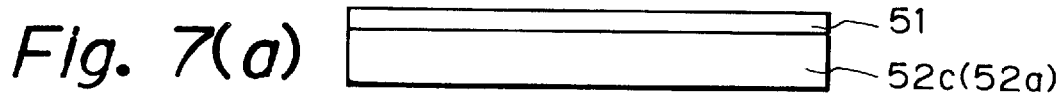
FIG. 7 illustrates diagrams for explaining a method of manufacturing a flat spiral coil and meander coil units for the electromagnetic acoustic transducer shown in FIG. 6 according to the present invention.

A method of manufacturing the spiral coil unit 5 of the electromagnetic acoustic transducer show in FIG. 6 will be explained with reference to FIGS. 7(a)–7(f). First, as illustrated in FIG. 7(a), a heat resistant insulating sheet (for example, a polyimide resin sheet) having a thickness of approximately 25 μm is cut into a predetermined outside dimension to form the insulation sheet 52c, and a copper foil 51 having a thickness of approximately 18–75 μm is adhered on one surface of the insulation sheet 52c. Another combination of the insulating sheet 52a and a copper foil 51 is also prepared.

Figure 7B:
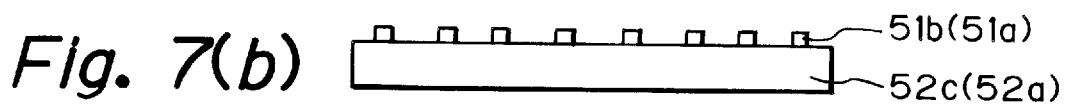

Second, as illustrated in FIG. 7(b), the copper foils 51 attached to the insulation sheets 51a, 51c are patterned to form the spiral coils 51a, 51b by etching. It will be of course understood by those skilled in the art that the coil patterns may be formed using conventional circuit printing techniques.

Figure 7C:
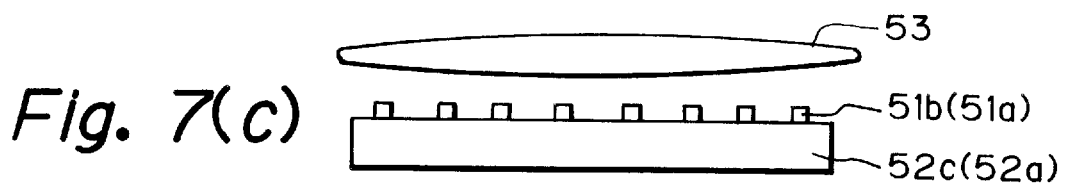

Then, heat resistant adhesive 53 is applied on the surfaces of the insulation sheets 52a, 52c on which the coils 51a, 51b have been patterned, as shown in FIG. 7(c). The adhesive also serves as insulators between adjacent patterns (lines) of the spiral coils, in addition to the adhesive for subsequently adhering an insulating sheet, later described. It is not always necessary to apply the adhesive on the surface of the sheet 52c.

Figure 7D:
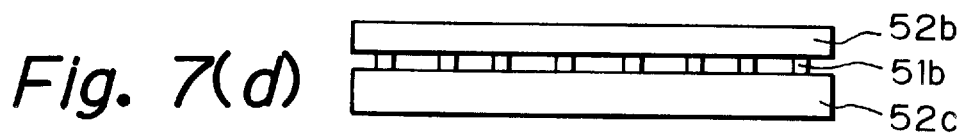
Figure 7E:
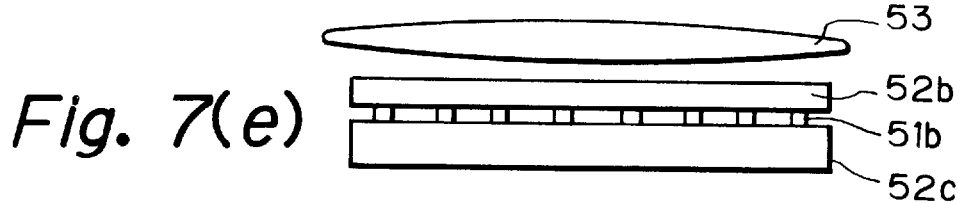
Figure 7F:
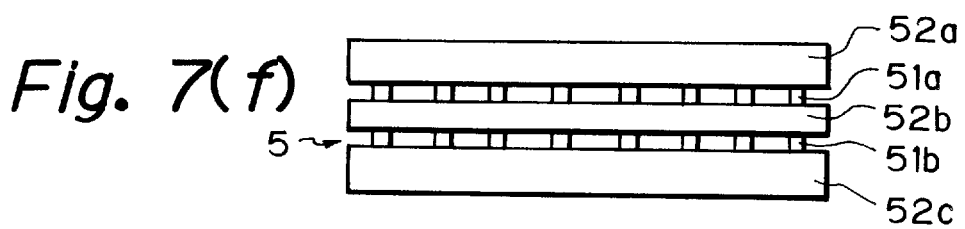

Next, as illustrated in FIG. 7(d), a heat resistant insulation sheet forming the insulation sheet 52b is adhered on the surface of the spiral coil 51b on the sheet 52c, then, as illustrated in FIG. 7(e), an adhesive 53 is applied on the upper surface of the insulating sheet 52b, and finally, as illustrated in FIG. 7(f), the insulation sheet 52a having the spiral coil 51a patterned thereon, created at the step shown in FIG. 7(c), is adhered on the adhesive 53 on the insulation sheet 52b, created at the step shown in FIG. 7(e), thus completing the flat spiral elongated coil unit 5.

As shown in FIG. 6(a), a first end of the spiral coil 51a is extending through a throughhole 54a formes through the insulation sheet 52a, and a first end of the spiral coil 51b is extending through a throughhole 54b formed through the insulation sheets 52a, 52b, to the upper surface of the coil unit 5, where they are connectable to external leads. The other ends of the spiral coils 51a, 51b are similarly extending through throughholes to the upper surface of the spiral coil unit 5 and are commonly connected to a ground. Since all the ends of the spiral coils are induced to the upper surface of the insulation sheet 52a or the coil unit 5, the bottom surface of the transducer, which faces an object to be inspected, can be made to be smooth.

A flat spiral coil unit 5 having the structure illustrated in FIG. 6 was fabricated based on the foregoing manufacturing method shown in FIG. 7. Exemplary dimensions of the fabricated flat spiral coil unit 5 were as follows. The outside dimension of the coil unit 5 or the insulation sheets 52a–52c had a length (L) of 40 mm and a width (W) of 25 mm. The insulation sheets 52a–52c had substantially the same thickness (H) of 0.025 mm. The spiral coils 51a, 51b between the insulation sheets had a width (W1) of 0.1 mm, an interval (L1) of 0.1 mm, and a thickness (H1) of 0.018 mm. The number of turns of the spiral coils were 44. (As to L, W, H, W1, L1 and H1, refer to FIG. 6(a).) The spiral coils 51a, 51b respectively had a resistance value of 50 Ω and an inductance of 40 $\mu$H. The fabricated flat spiral coil unit had a sufficient sensitivity in practical for an electromagnetic acoustic transducer.

According to the ultrasonic transducer of the present invention described with reference to FIGS. 6 and 7, it is possible to realize improved performance, stability, uniform quality, reduction in size, finer structure, reduction in manufacturing time, and enhanced functionality (increased S/N ratio) by an ideal parallel coil.

That is, since the insulation sheet 52b can be made of a heat resistant insulation material of, for example, polyimide, having a thickness of approximately several 10 microns, and the spiral coils 51a, 51b respectively serving as reception and transmission coils can be positioned opposite to and coincide (overlapping) with each other through the insulation sheet 52b, reflection waves of transmitted ultrasonic shear waves from the transmitter coil can be captured by the receiver coil at the same position, thus making it possible to make accurate measurements.

Further, since the spiral coils can be fabricated with an accurately defined coil interval L1 by using a circuit printing technique, stable ultrasonic waves can be received. The use of the insulation adhesive 53 for adhering the insulation sheets to the spiral coils enables the adjacent wires of the spiral coils to be insulated from each other. Accordingly, the flat spiral coil unit can be employed in an inspection system wherein a power of approximately 1000 volts is supplied.

In addition thereto, since the spiral coils are arranged on the opposing surfaces of the insulation sheet 52b, a smaller and finer coil structure can be provided, as compared with a conventional spiral coil fabricated by manually winding cladded copper wires such as enamel wires on a surface of a sheet, and the insulation sheet 51a, 51c positioned the outer sides of the coil unit 5 also serves as protective films. Further, since all the ends of the spiral coils for connecting to external circuits are lead to the upper surface of the coil unit, the lower surface thereof can be obtained with no rugged portion and thus it can be face an object with a uniform distance.

Figure 3:
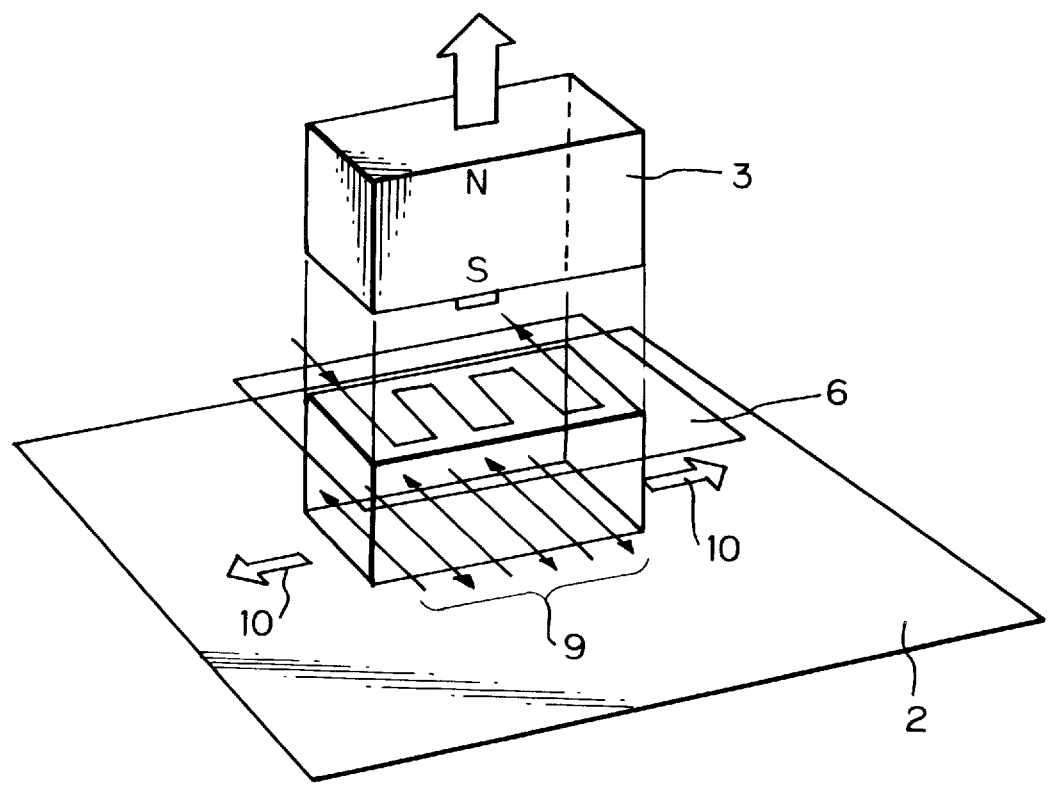
FIG. 3 schematically shows an inspection system using a meander coil type electromagnetic acoustic transducer according to a prior art.
Figure 8A:
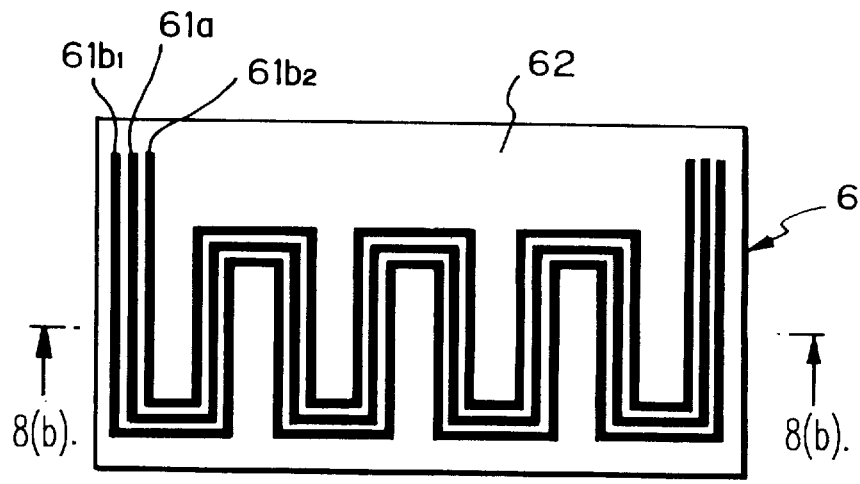
FIG. 8(a) is a plan view schematically illustrating a meander coil sheet unit for use in a meander coil type electromagnetic acoustic transducer according to the present invention.
Figure 8B:
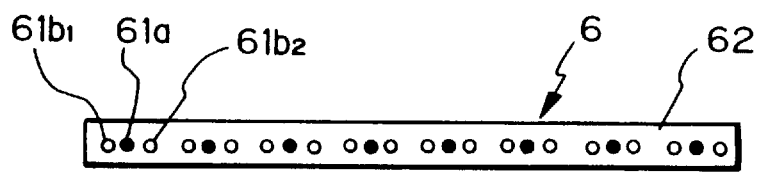
FIG. 8(b) is a cross-sectional view taken along a line A—A of FIG. 8(a)

FIGS. 8 shows an example of a meander coil unit 6 according to the present invention, which can be employed in an electromagnetic acoustic transducer of an inspection system as shown in FIG. 3. FIG. 8(a) is an explanatory top plan view of the meander coil unit 6, and FIG. 8(b) is a cross-sectional view taken along a line A—A of FIG. 8(a). As illustrated, the meander coil unit 6 is fabricated by aligning three meander enamel wires 61a, 61$b_1$, 61$b_2$ close to each other by hand, and patterning the enamel wires appropriately to a particular object to be inspected while solidifying the enamel wires with a resin to form a resin sheet 62. The meander coil unit 6 is so flexible to bend.

The central wire 61a within the three meander wires is used as a transmitter coil for generating ultrasonic waves according to an electromagnetic action, and the remaining two outside wires 61$b_1$, 61$b_2$ are used as receiver coils having an ultrasonic wave detection function. By thus separately providing the transmitter coil 61a and the receiver coils 61$b_1$, 61$b_2$, the S/N ratio and the gain can be increased.

Figure 10A:
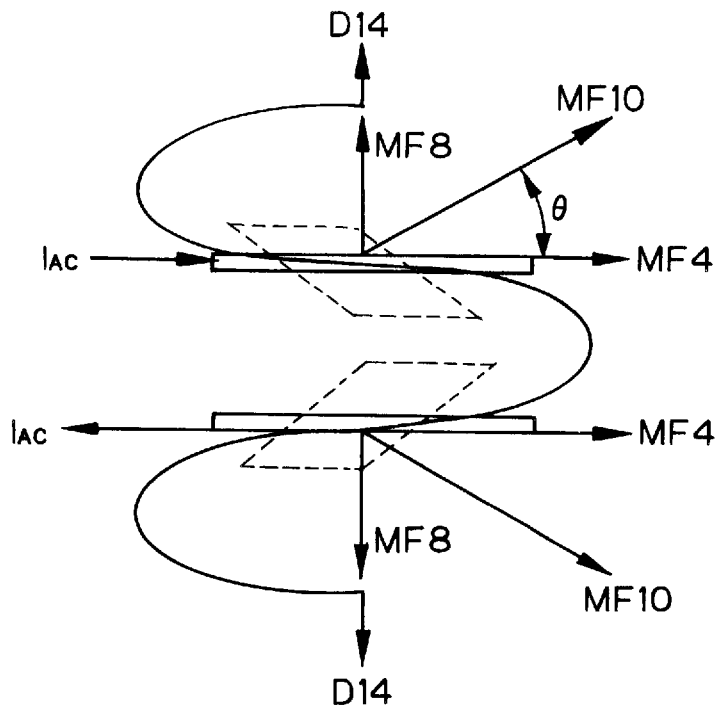
FIG. 10 shows diagrams for explaining the measuring principles by the inspection system using a meander coil type electromagnetic acoustic transducer.
Figure 10B:
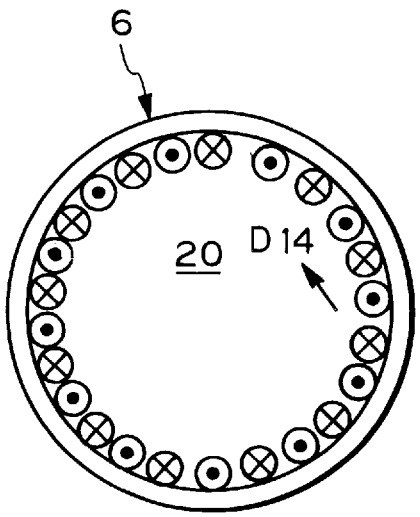

FIG. 9 is a diagram of an inspection system for a cylindrical object 20 in which the meander coil unit 6 shown in FIG. 8 is used. The system further includes a solenoid coil 3, pre-amplifier 16, main amplifier 17, controller 18, and DC power supplier 40. FIG. 10 illustrates behaviors on the surface of the cylindrical object 20 beneath the meander coil unit 60. Although FIG. 9 illustrates only a meander line of the meander coil unit 6, the line represents the band of the meander coils 61a, 61$b_1$, 61$b_2$. In the inspection system shown in FIG. 9, an electromagnetic acoustic transducer comprises the solenoid coil 3 and the meander coil unit 6. A DC current $I_{DC}$ is applied to the solenoid coil 3 from the DC power supplier source 40 to magnetize the cylindrical object 20 with a static magnetic field MF4. Subsequently, a rf burst current $I_{AC}$ is applied from the controller 18 to the meander coil unit 6 surrounding the cylindrical object 20 to generate an alternate magnetic field MF8 on the surface of the object 20 beneath parallel lines, or the parallel bands of the wires or coils 61a, 61$b_1$, 61$b_2$ of the meander coil unit 6, in the direction perpendicular to that of the static magnetic field MF4, as illustrated in FIG. 10(a). Thus, a combined magnetic field MF10 is generated at an angle θ relative to the direction of the static magnetic field MF4.

Figure 10C:
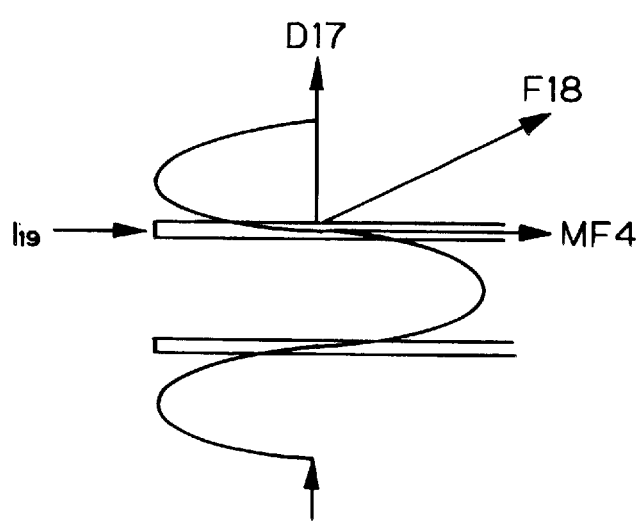

Referring further to FIG. 10(a), in adjacent areas beneath the parallel bands of the meander coil unit 60, the directions of the combined magnetic field MF10 at the respective areas are symmetric to the direction of the static magnetic field MF4. Thus, micro areas of the object 20 under the parallel bands are subjected to shear deformation due to a magnetostrictive effect. As the direction of the alternate magnetic field MF8 changes, ultrasonic waves (axially symmetric SH waves) are generated and travel in a direction indicated by arrows D14. When the ultrasonic waves reach end faces of damages, defects, grain boundaries, structural changes, and so on on the surface and in the interior of the object 20, they are reflected therefrom in the direction D17 as shown in FIG. 10(c). When the reflected ultrasonic waves reach the vicinity of the surface of the cylindrical object 20, a force F18 is generated, and a current $I_{19}$ is generated by an interaction of the force F18 and the static magnetic field MF4. The current $I_{19}$ is detected by the receiver coil 61$b_1$, 61$b_2$, amplified by the pre-amplifier 16, further amplified by the main amplifier 17, and sent to the controller 18. The controller 18 analyzes the current $I_{19}$ which has been amplified to measure damages, defects, grain boundaries, structural changes and so on on the surface and in the interior of the object 20.

It is of course that the meander that coil unit 6 shown in FIG. 8 can be used to inspect such a plane object 2 as shown in FIG. 3.

Figure 11A:
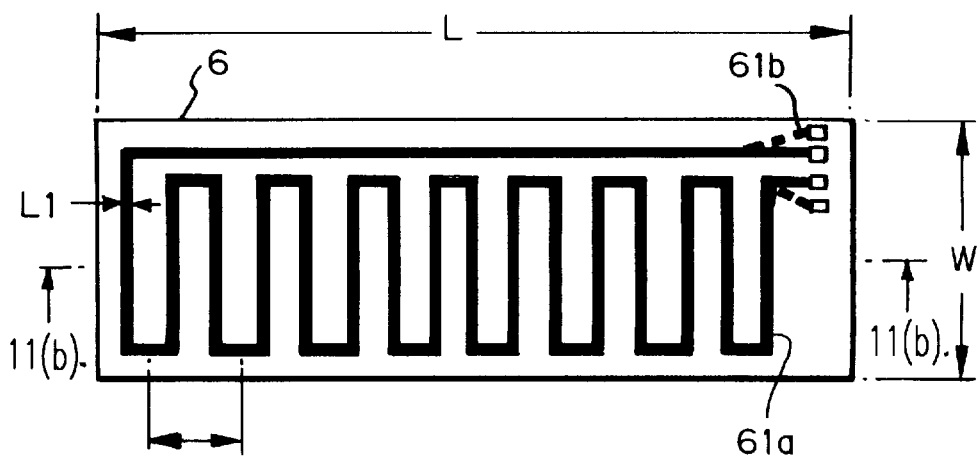
FIG. 11(a) is a top plan view schematically illustrating a meander coil sheet unit for use in a meander coil type electromagnetic acoustic transducer according to the present invention.
Figure 11B:
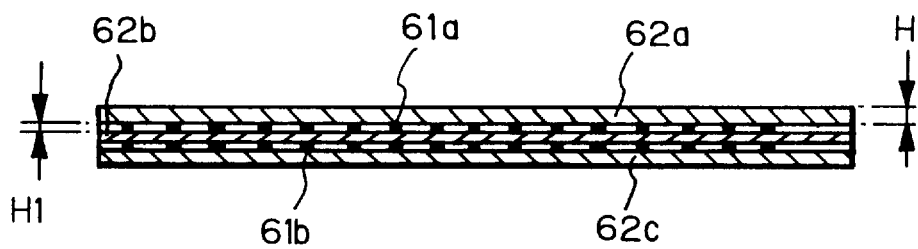
FIG. 11(b) is a cross-sectional view taken along a line A—A of FIG. 11(a)

FIG. 11 illustrates another meander coil unit 6 according to the present invention, which is usable in the inspection system shown in FIG. 9, wherein FIG. 11(a) is a top plan view of the meander coil unit 6, and FIG. 11(b) is a cross-sectional view taken along a line A—A of FIG. 11(a). The meander coil unit 6 of this embodiment comprises a meander coil 61a and a meander coil 61b, both made of an electrically conductive material, formed on the opposing surfaces of an insulation sheet 62b made of heat resistant resin (for example, polyimide) using etching or printing techniques. The meander coils 61a, 61b are positioned opposite to and coincident with each other through the insulation sheet 62b. Also, an insulation sheets 62a, 62c are adhered on each of the surfaces of the meander coils 61a, 61b with a heat resistant and insulating adhesive.

One of the meander coil 61a, 61b serves as a transmitter coil for emitting ultrasonic waves, and the other one serves as a receiver coil having a detecting function. Since electromagnetic acoustic transducers generally have better receiver characteristics than transmission characteristics, the transmitter coil is preferred to be positioned nearer an object. The meander coil unit 6 shown in FIG. 11 can be also employed to inspect a flat object 2 as shown in FIG. 3. The ends of the meander coils 61a, 61b shown in FIG. 11 are extending through throughholes to the upper surface of the unit 6, similarly to those of the spiral coil 5 shown in FIG. 6.

The meander coil unit 6 shown in FIG. 11 is also fabricated similarly to that of the spiral coil unit 5 shown in FIG. 6, though the coil patterns are different.

A meander coil unit 6 having the structure illustrated in FIG. 11 was fabricated based on the manufacturing method similar to that shown in FIG. 7. Exemplary dimensions of the meander coil unit 6 are as follows. The outside dimension of each of the insulation sheets 62a–62c have a length (L) of 44.5 mm, a width (W) of 25 mm, and a thickness (H) of 0.025 mm. The meander coils 61a, 61b have a width (L1) of 0.11 mm, a pitch (W1) of 0.9 mm, and a thickness (H1) of 0.025 mm. The number of meandering lines is 48. The meander coils 61a, 61b respectively have a resistance value of 12 Ω and an inductance of 1 $\mu$H, thus being provided a meander coil unit 6 for a transducer practically having a sufficient sensitivity.

The employment of the meander coil as illustrated in FIG. 11 to a meander coil type electromagnetic acoustic transducer results in the following beneficial effects.

First, the insulation sheet 62b is a heat resistant insulating sheet of, for example, polyimide, having a thickness of approximately several-ten microns, and the meander coil 61a, 61b serving as receiver and transmitter coils are positioned opposite to and coincide (overlapping) with each other through the insulation sheet 62b, so that reflected waves of transmitted waves from the transmitter coil can be captured by the receiver coil at the same position, thus making it possible to make accurate measurements, as compared with the meander coil unit 6 shown in FIG. 8.

Second, since the meander coils 61a, 61b are fabricated with an accurately defined coil pitch W, as compared with coils formed of manually wound wires, stable ultrasonic waves can be received.

Third, the use of the insulation adhesive for adhering the insulation sheets enables adjacent portions of each of the meander coils 61a, 61b to be insulated from each other, with the result that the finished transducer can resist an applied voltage of approximately 1000 volts during measurements.

Fourth, since the meander coils are arranged on the opposing surfaces of the insulation sheet 62b, it is possible to provide uniform quality, reduction in size, finer structure, reduction in manufacturing time, and enhanced functionality (increased S/N ratio) by an ideal parallel coil, as compared with coils fabricated by winding cladded copper wires such as enamel wires or the like by hand.

Fifth, the meander coil unit 6 is planarized (formed into a sheet) so that it is flexible, and a rugged portion between an object to be inspected and the meander coil unit 6 is eliminated.

Figure 12:
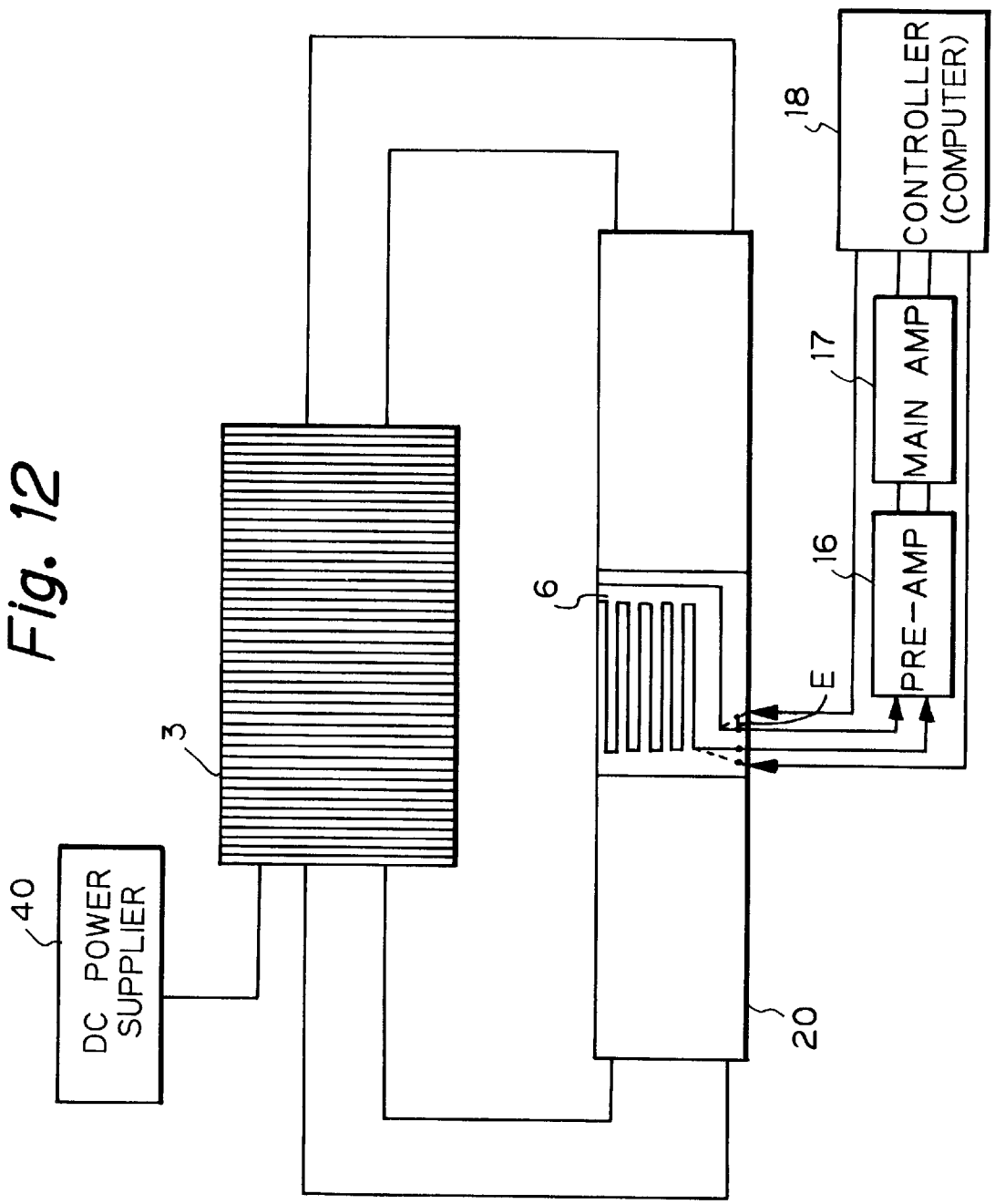

FIG. 12 illustrates a second embodiment of an inspection system using the meander coil unit 6 shown FIG. 8 or 11, according to the present invention. The meander coil unit 6 is positioned on the circumferential surface of a cylindrical object 20. A core 24, made of a magnetic material, extends through the internal space of a solenoid coil 3 for generating a static electric field and through the internal space of the cylindrical object 20 to form a magnetic circuit. Then, a static magnetic field is generated in the axial direction of the object 20 to generate ultrasonic waves (axially symmetric SH waves). In FIG. 12, the symbol "E" denotes a ground terminal.

Figure 13:
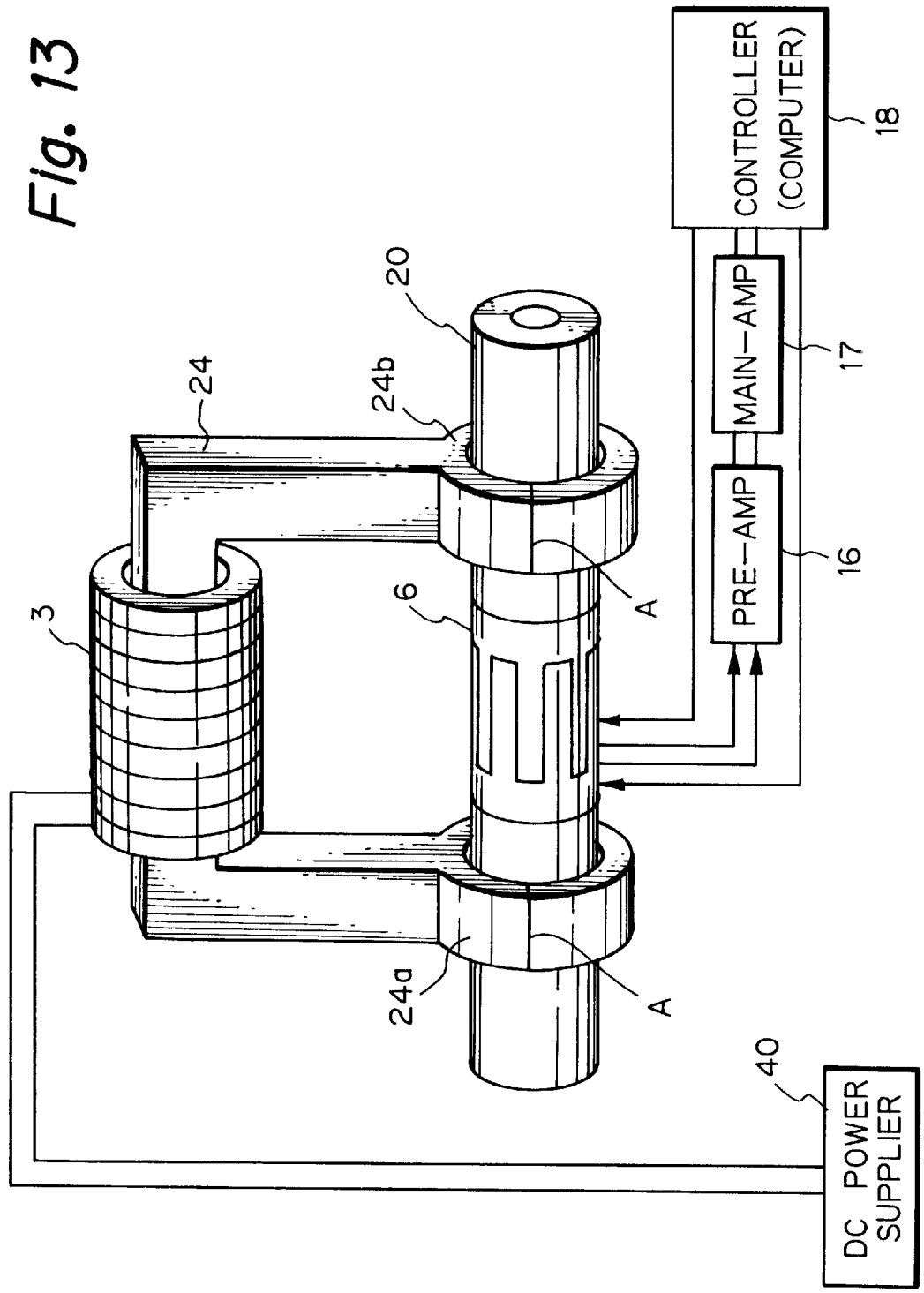

FIG. 13 shows a third embodiment of an inspection system using the meander coil unit 6 shown FIG. 8 or 11, according to the present invention. In the system, a core 24 extending through a solenoid coil 3 and magnetically connecting the coil 3 with a cylindrical object 20, is constituted as a U-shape to have open ends where toroidal (annular) portions 24a, 24b are formed. Each of the toroidal portions 24a, 24b can be divided into an upper half and a lower half along a central portion thereof (indicated by a solid line A). Thus, when the object 20 is to be mounted, the lower halves are removed to fit the object 20 into recesses of the upper halves, and then the lower halves are coupled to the upper halves with a suitable means, not shown. With the toroidal portions 24a, 24b having the structure described above, even if the cylindrical object 20 has both ends with a diameter larger than the inner diameter of the toroidal portions so that the object 20 cannot be passed through the toroidal portions 24a, 24b, the object can be readily mounted in the toroidal portions.

A meander coil unit 6 shown in FIG. 6 or 11 is placed on the circumferential surface of the cylindrical object 20 to generate a static magnetic filed in the longitudinal direction of the object so as to generate ultrasonic waves (axially symmetric SH waves).

Figure 14:
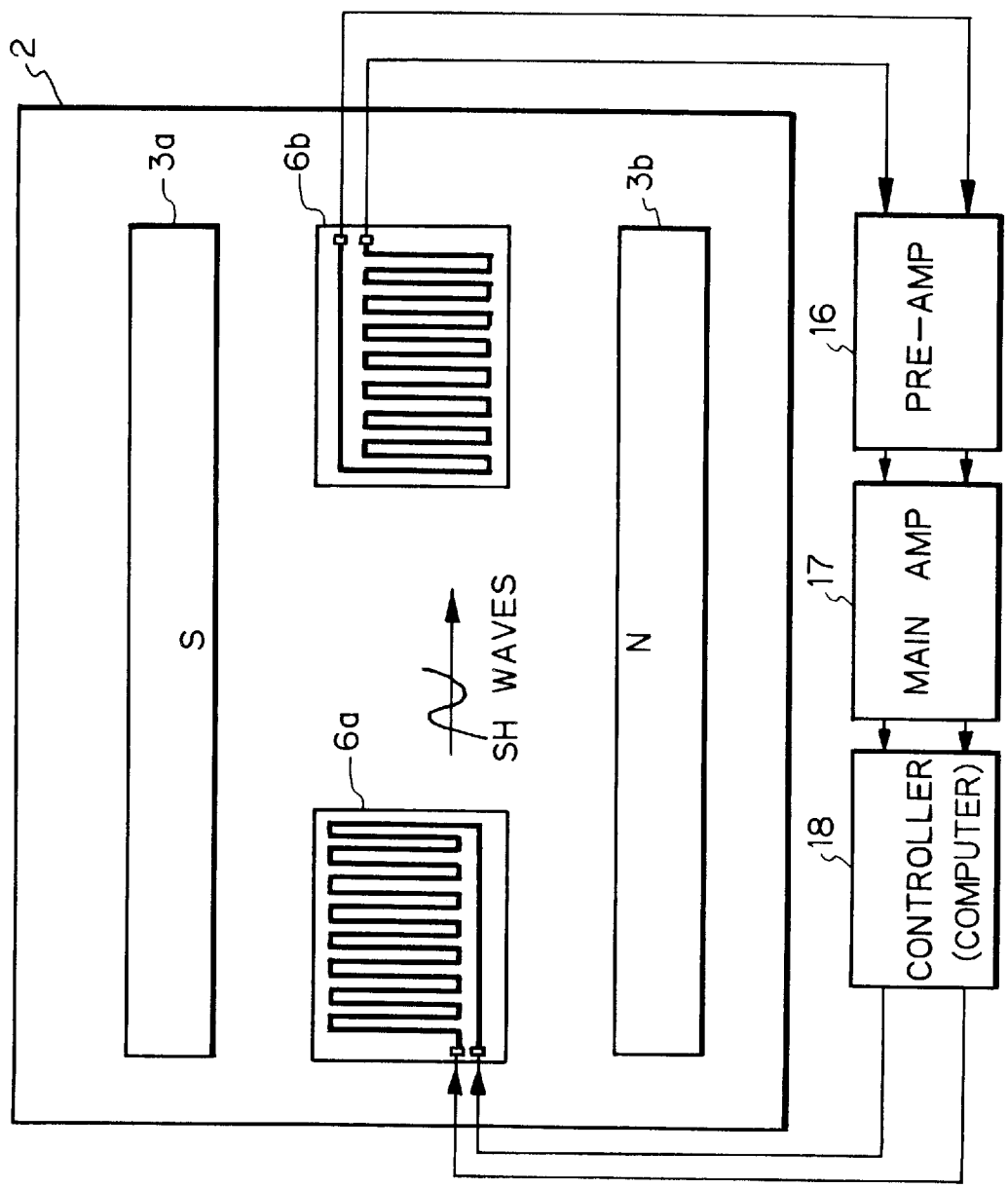

FIG. 14 illustrates a third inspection system according to the present invention wherein an electromagnetic acoustic transducer has a pair of the meander coil units shown in FIG. 11. As the units, the meander coil units 6 shown in FIG. 8 is also usable. In FIG. 14, the meander coil units are denoted by the symbol "6a" and "6b". A pair of permanent magnets (or electromagnets) 3a, 3b for generating a static magnetic field are positioned on a plate-like object 2, with a predetermined spacing therebetween, so as to generate the static magnetic field around the central area therebetween in the axial direction of thereof. The meander coil units 6a, 6b are placed between the permanent magnets 3a, 3b with a predetermined spacing therebetween in, the axial direction of the magnets 3a, 3b. One of the meander coil units 6a, 6b is used for transmitting and the other for receiving. In FIG. 14, the left-hand meander coil unit 6a is used for transmitting of ultrasonic wave (surface SH wave), and the right-hand meander coil unit 6b is used for receiving, in FIG. 14.

Figure 15:
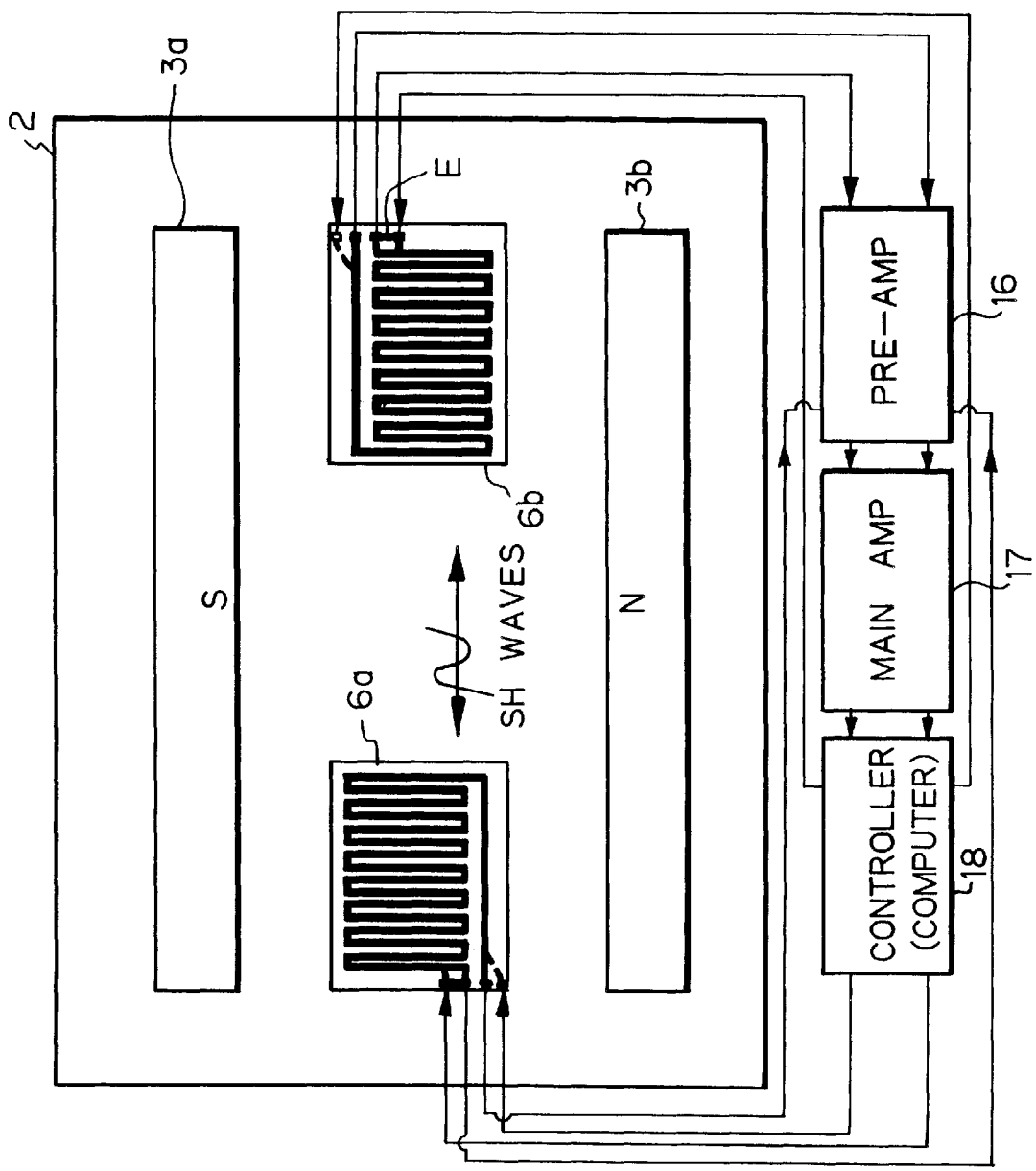

Instead of using the meander coil units 6a, 6b as shown FIG. 14, both the units can be used for transmitting and receiving. In this case, ultrasonic waves are generated simultaneously from both the meander coil unit 6a, 6b and received simultaneously by both, so that the S/N ratio can be increased. FIG. 15 shows a fourth embodiment of an inspection system according to the present invention wherein both meander coil units 6a, 6b, each having the constitution shown in FIG. 11, are used for transmitting and receiving. The lower coils of the meander coil units 6a, 6b are applied with a voltage form a controller 18 such that ultrasonic waves are simultaneously transmitted from both the coil units 6a, 6b, and the upper coils thereof receives the transmitted ultrasonic waves. With this configuration, the sensitivity is further improved. It is of course the matter that meander coil unit each having the structure shown in FIG. 8 can be also used as the meander coil units 6a, 6b in the fourth embodiment.

Figure 17A:
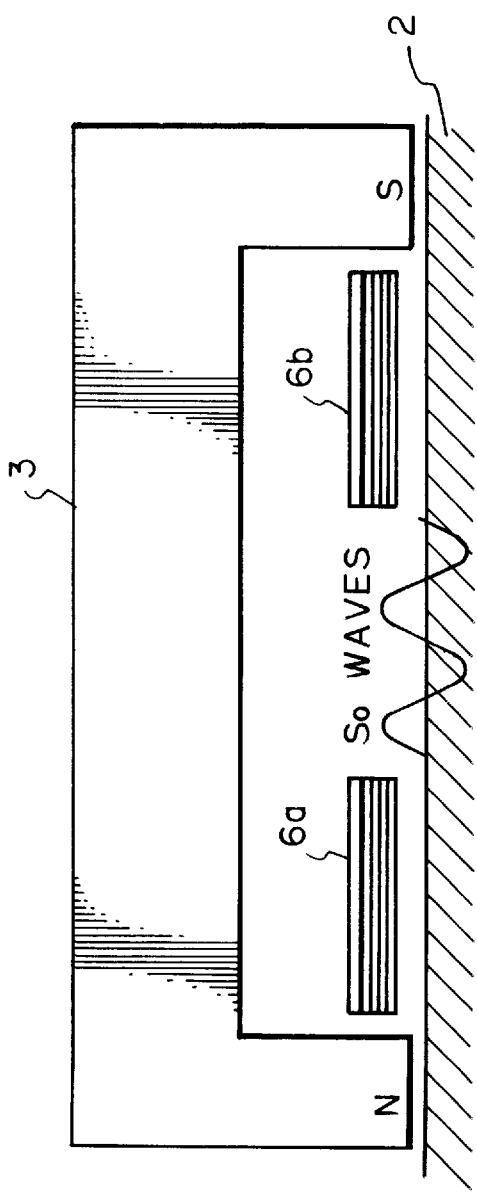
Figure 17B:
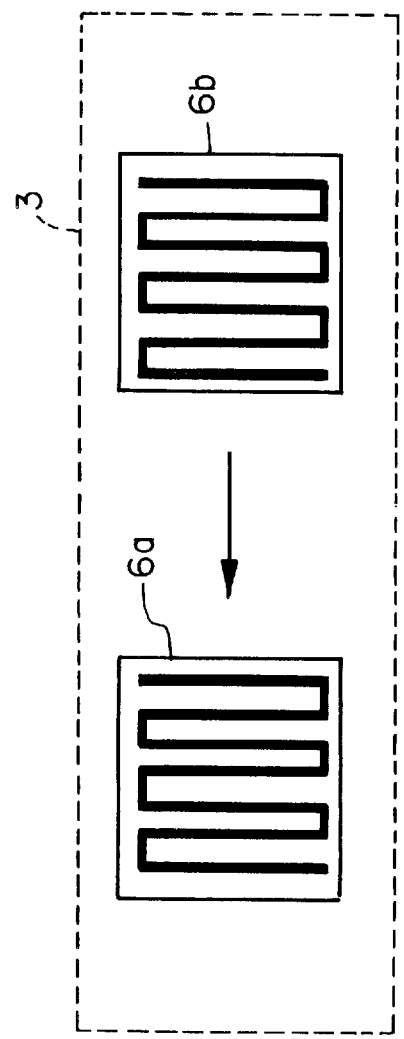

FIGS. 16 and 17 illustrate fifth and sixth embodiments of an inspection system according to the present invention wherein a pair of meander coil units 6a, 6b having the structure shown in FIG. 11 are incorporated. FIGS. 16(a) and 17(a) are front views of the embodiments each for showing a positioning relationship between a permanent magnet (or electromagnet) 3 and the meander coil units 6a, 6b in a front view, and FIGS. 16(b) and 17(b) are top plan views for showing the same positional relationships. In the system shown in FIG. 17, the magnet 3 is constituted to have a U-shape.

In each of the systems shown in FIG. 16 or 17, the magnet 3 is positioned above an object 2 to be inspected to generate a static magnetic field in the thickness direction (FIG. 16) and longitudinal direction (FIG. 17) of the object 2 and the meander coil units 6a, 6b are positioned between the object 2 and the permanent magnet (or electromagnet) 3 with a predetermine spacing therebetween. One of the meander coil units 6a, 6b is used for transmitting, and the other for receiver. In FIGS. 16 and 17, the right-hand meander coil unit 6b is represented as a transmission unit for transmitting ultrasonic wave (SO wave) signals to the left-hand meander coil unit 6a.

Since the connections of the meander coil units 6a, 6b with a controller, a main amplifier, and a pre-amplifier in the fifth and sixth embodiments are substantially the same as those illustrated in FIGS. 9, 12–15, the illustration of these components is omitted in FIGS. 16 and 17. It should be noted that in the meander coil units 6, 6a, 6b employed in the system shown in FIGS. 9 and 12–17, the earth ends E of the transmitting and receiving meander coils of the respective coil units are connected to each other.

In the inspection system shown in FIGS. 9 and 12–17 using the meander coil type electromagnetic acoustic transducers, the transducer illustrated in FIG. 16 utilizes a Lorentz force as an excite force for generating ultrasonic waves, while the remaining transducers utilizes a magnetostrictive force as the excite force.

According to the electromagnetic acoustic transducers employing the meander coil units shown in FIGS. 8 and 11, since the meander coil units have the separate transmitting meander coil and receiving meander coil, a higher S/N ratio and a larger gain can be accomplished, and since they have a high flexibility they can be employed to inspect cylindrical objects.

Using the meander coil unit shown in FIG. 11, since the meander coils are positioned on the opposing surfaces of the middle insulation sheet so as to face each other and they can be easily formed as ideal parallel coils, it is possible to realize improved performance, stability, uniform quality, reduction in size, finer structure, reduction in manufacturing time, and enhanced functionality (increased S/N ratio), which cannot be accomplished by conventional electromagnetic acoustic transducers.

Next, another inspection system according to the present invention which employs an electromagnetic acoustic transducer and predicts fatigue life relying on electromagnetic acoustic resonance will be explained with reference to FIG. 18. The system basically comprises the same components as shown in FIG. 1, and further includes a computer 19.

Figure 18:
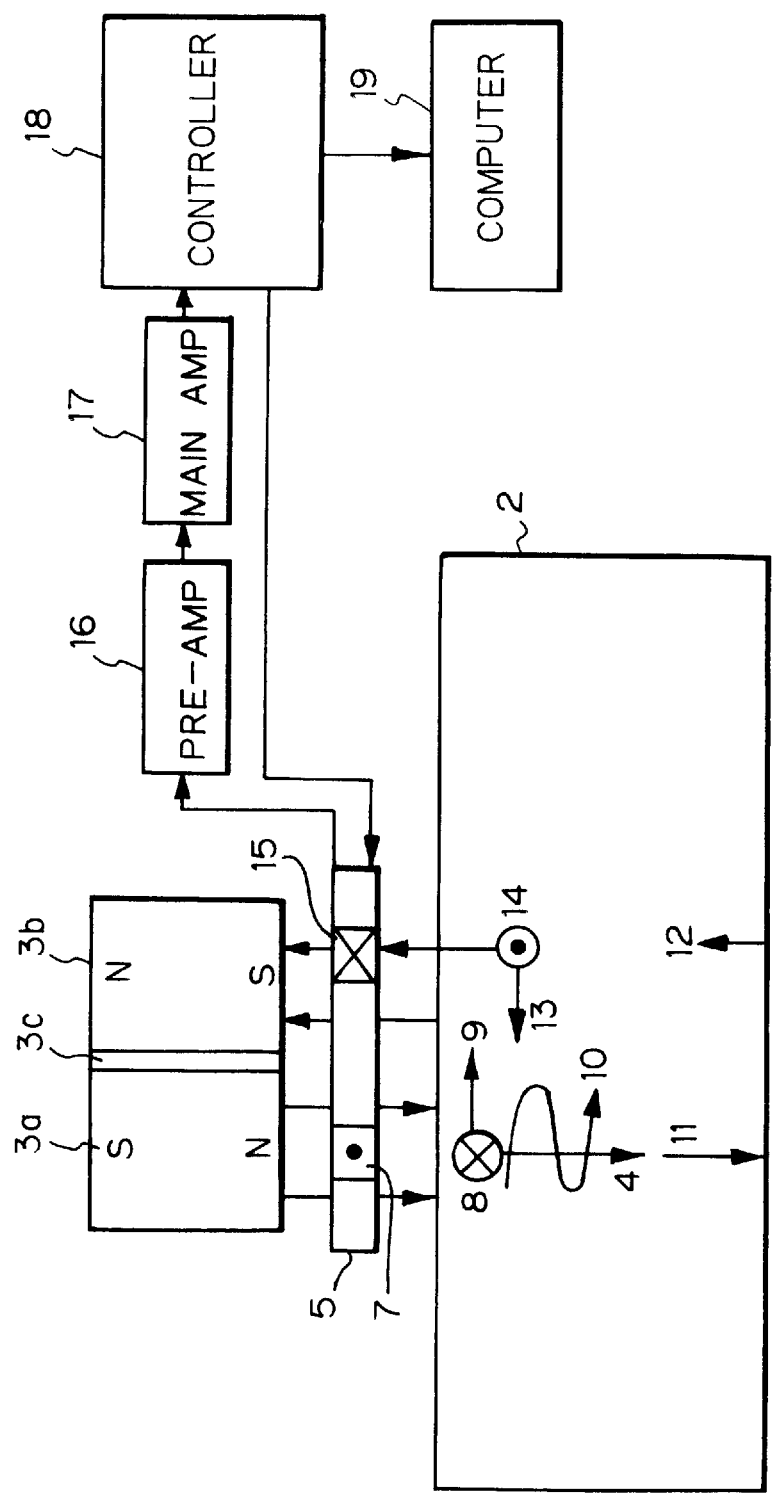
FIG. 18 shows an inspection system for predicting a fatigue life based on an electromagnetic acoustic resonance method, according to the present invention.

As illustrated in FIG. 18, the inspection system or lifetime prediction system includes a pair of permanent magnets (or electromagnets) 3a, 3b, a flat spiral coil unit 5, a pre-amplifier 16, a main amplifier 17, a controller 18, and the computer 19. The meander coil type EMAT can be also applied to the system.

As has been explained with reference to FIG. 1, when a rf burst current 7 is applied from the controller 18 to the flat spiral coil unit 5, the eddy current 8 is generated in the object 2 in the direction opposite to that of the high frequency current, and a Lorentz force 9 is generated by an interaction of the eddy current 8 and a static magnetic field 4 generated by the magnets 3a, 3b, in accordance with the Fleming's left hand law.

The Lorentz force 9 acts on internal free electrons inside the object 2 to cause collision with ions and so on, and induce movements perpendicular to the direction of the static magnetic field 4 and the eddy current 8 to generate ultrasonic shear waves 10. The ultrasonic shear waves 10 travel in a direction indicated by the arrow 11, propagate on the surfaces and in the interior of the object 2, in which organizational changes, micro-cracks, and so on have occurred due to fatigue, and reflect on the opposing surface of the object 2. When the ultrasonic shear waves 10 reach near the upper surface of the object 2 by travelling in the direction indicated by the arrow 12, a force 13 is generated. An eddy current 14 is generated by an interaction of this force 13 and the static magnetic field 4.

The eddy current 19 is detected by the flat spiral coil unit 5. The detected signal representative of the eddy current 14 is amplified by the pre-amplifier 16 and the main amplifier 17, and sent to the controller 18. Further, the signal is provided from the controller 18 to the computer 19. The controller 18 comprises a super-heterodyne measuring system which can make a measurement in a short time because it only requires amplitude and phase of the detection signal.

The principles of the electromagnetic acoustic resonance method will be explained. When the rf burst current provided to the flat spiral coil unit 5 from the controller 18 is a burst high frequency current having a constant amplitude and a constant frequency), the ultrasonic shear waves 10 are burst waves. The burst ultrasonic waves 10 repeatedly reflect on opposing surfaces of the object 2, and when the ultrasonic waves reach an incident plane, the coil unit 5 detects the burst waves as the eddy current.

If a cycle of the burst waves is longer than a time required for the ultrasonic shear waves 10 to ply to propagate back and fourth within thickness direction of the object 2, the reflected signals received by the coil unit 5 overlap. Since the reflected signals simultaneously received at the coil unit 5 are individual propagation time periods (=individual propagating distances/an ultrasonic wave speed), the reflected signals generally differ in phase from each other. As a result, interference occurs in the overlapping reflected signals. More specifically, if the overlapping reflected signals are coincident in phase, peaks and valleys of the respective signals overlap to intensify each other. On the contrary, if the overlapping reflected signals differ in phase, peaks and valleys of the respective signals offset each other so that the signals become smaller. Thus, by adjusting the burst wave cycle such that a propagation time period required for the ultrasonic shear waves to propagate back and fourth within thickness direction of object 2 is an integer multiple of the burst wave cycle, a composite wave having large interference can be provided. The condition mentioned above is referred to as "ultrasonic resonance".

Since the electromagnetic acoustic transducer has an extremely low transduce efficiency, only minimum energy at a receiving stage is transduced into an electric signal, so that the propagation of the ultrasonic waves in the object is not affected. In the system shown in FIG. 18, the ultrasonic resonance is caused by the electromagnetic acoustic transducer (or, the magnets 3a, 3b, and coil unit 5) under a control of the controller 18, to predict fatigue life of the object 2.

Figure 19:
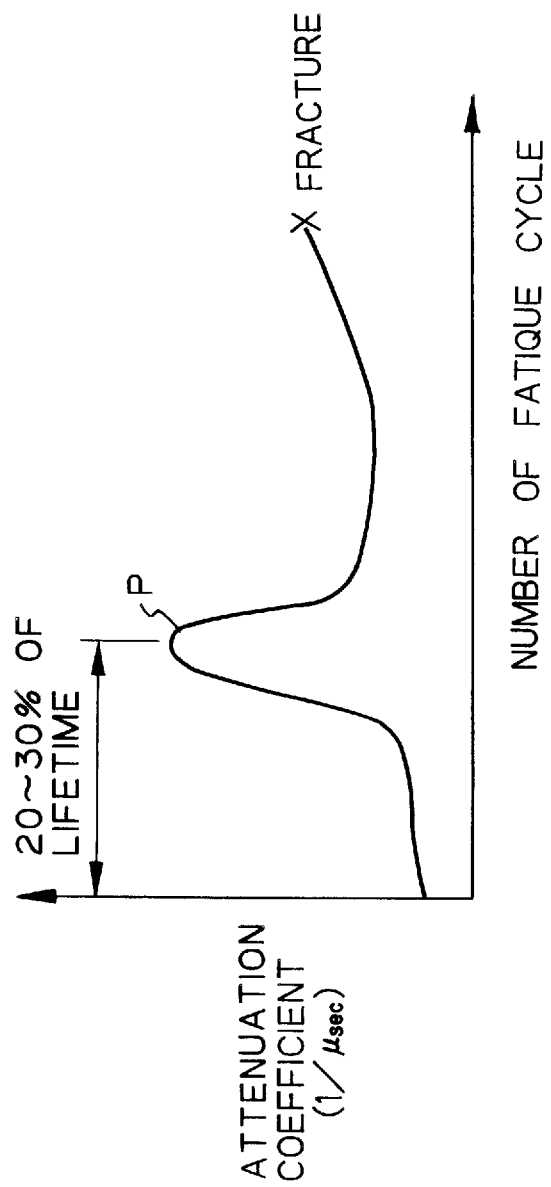
FIG. 19 is a graph representing an example of a change of attenuation in a fatigue progress measured with the electromagnetic acoustic resonance method.

In the fatigue life prediction system, a resonance frequency and attenuation characteristics are accurately measured at every measurement sampling time, and a fatigue progress is monitored by comparing the detected attenuation characteristics with a database in the computer 19 containing an attenuation characteristic curve experimentally obtained. FIG. 19 represents an attenuation characteristic curve, that is a relationship of an attenuation coefficient to the number of repetitions (or number of repetitions/number of times of fatigue rupture), stored in the database.

As shown in FIG. 19, the attenuation coefficient exhibits a peak value P at 20–30% of the fatigue, and abruptly drops after the peak, followed by a gradual increase till rupture. The peak value P corresponds to occurrence of fatigue crack. Thus, the fatigue life prediction system according to the present invention takes advantage of the behavior of such a peak value P regarding the object 2 to accurately measure lifetime thereof and assess the fatigue damage. Further, from the fact that an increasing ratio of the attenuation coefficient is extremely small in a range such as below a fatigue limit, the changing ratio of the attenuation coefficient is monitored to predict that fatigue fracture will not occur.

If the database does not contain a corresponding condition, an estimation is made using a known neural network approach to create an attenuation curve associated with the condition.

Figure 20:
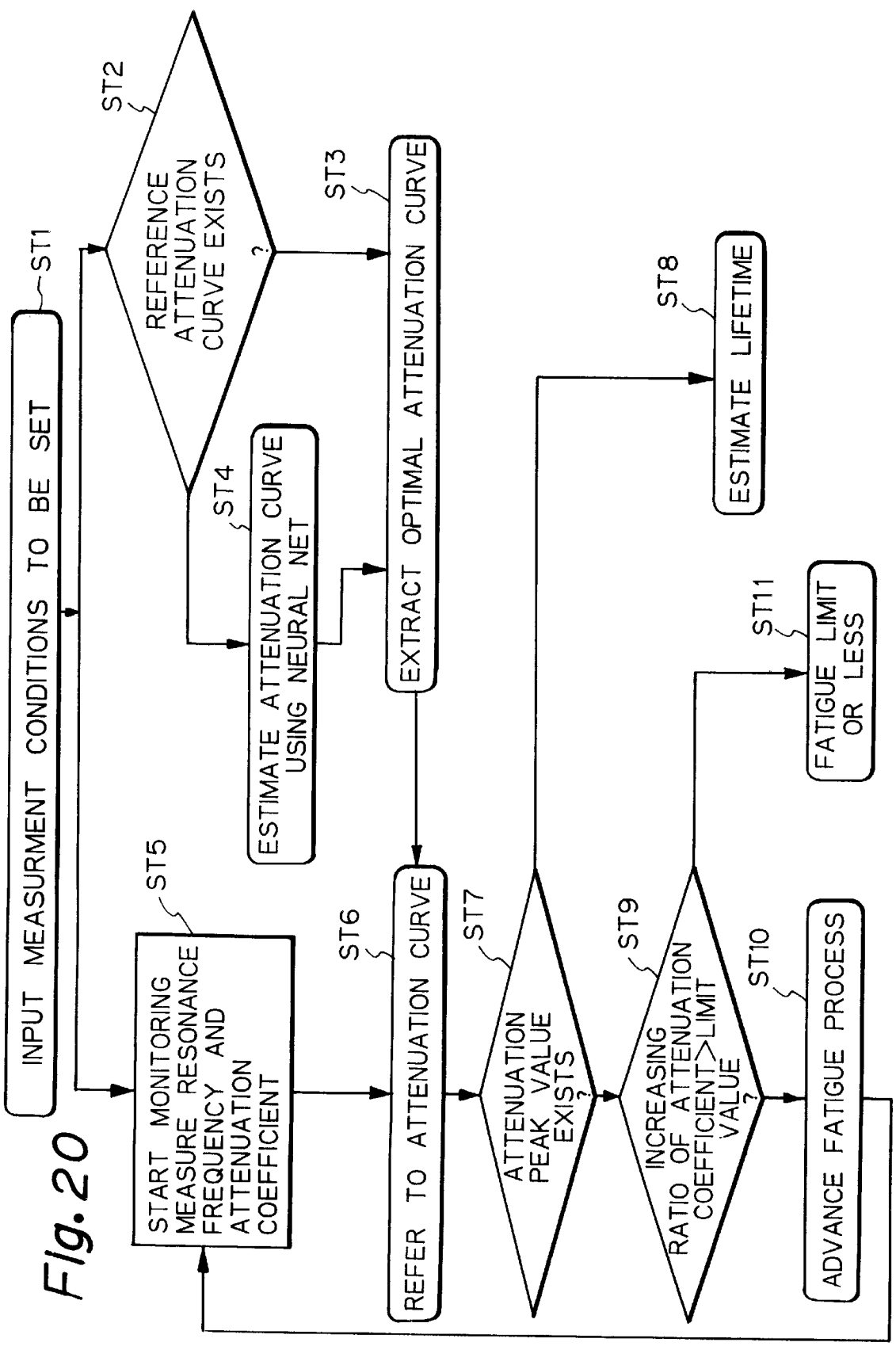
FIG. 20 is a flow chart illustrating a flow of operations for measuring fatigue and estimating lifetime based on the electromagnetic acoustic resonance, according to the present invention.

FIG. 20 is a flow chart illustrating a flow of operations performed for measuring fatigue damage and estimating lifetime of the object 2 in the system shown in FIG. 18, in accordance with the present invention. First, material characteristics (a sonic speed in the material and so on) of the object 2, measurement conditions including a resonance frequency, a range, and so on are inputted (step ST1). Attenuation curves in the database are referenced based on the inputted data to confirm whether or not the database has an attenuation curve corresponding to the set conditions (step ST2). If YES, an optimal attenuation curve is extracted from the database (ST3). If NO, the neural network approach is used to estimate an attenuation curve appropriate to the set conditions (step ST4).

Subsequently, an attenuation coefficient is measured at a resonance frequency which is also measured by the system (step ST5), and the attenuation curve extracted from the database or estimated using the neural network approach is referenced with the measured attenuation coefficient value (step ST6) to confirm a damaged condition and to check whether or not the attenuation coefficient indicates a peak value P of the extracted or estimated attenuation curve (step ST7). If the peak value is indicated, a fatigue life ratio is calculated from the attenuation curve to derive remaining life and lifetime (step ST8).

If the measured attenuation coefficient is not indicated the peak value P at step ST7, the monitoring is continued. While the monitoring, it is checked whether or not an increasing ratio of the measured attenuation coefficient is equal to or larger than a limit value (increasing ratio of attenuation coefficient>limit value) (step ST9). If the increasing ratio is smaller than the limit value, the fatigue process is advanced (step ST10) and the monitoring is continued. If the increasing ratio is larger than the limit value, i.e., if the increasing ratio has exceeded the limit value, a peak value P is estimated from the attenuation curve in the database and the measurement results using the neural network approach.

Figure 21:
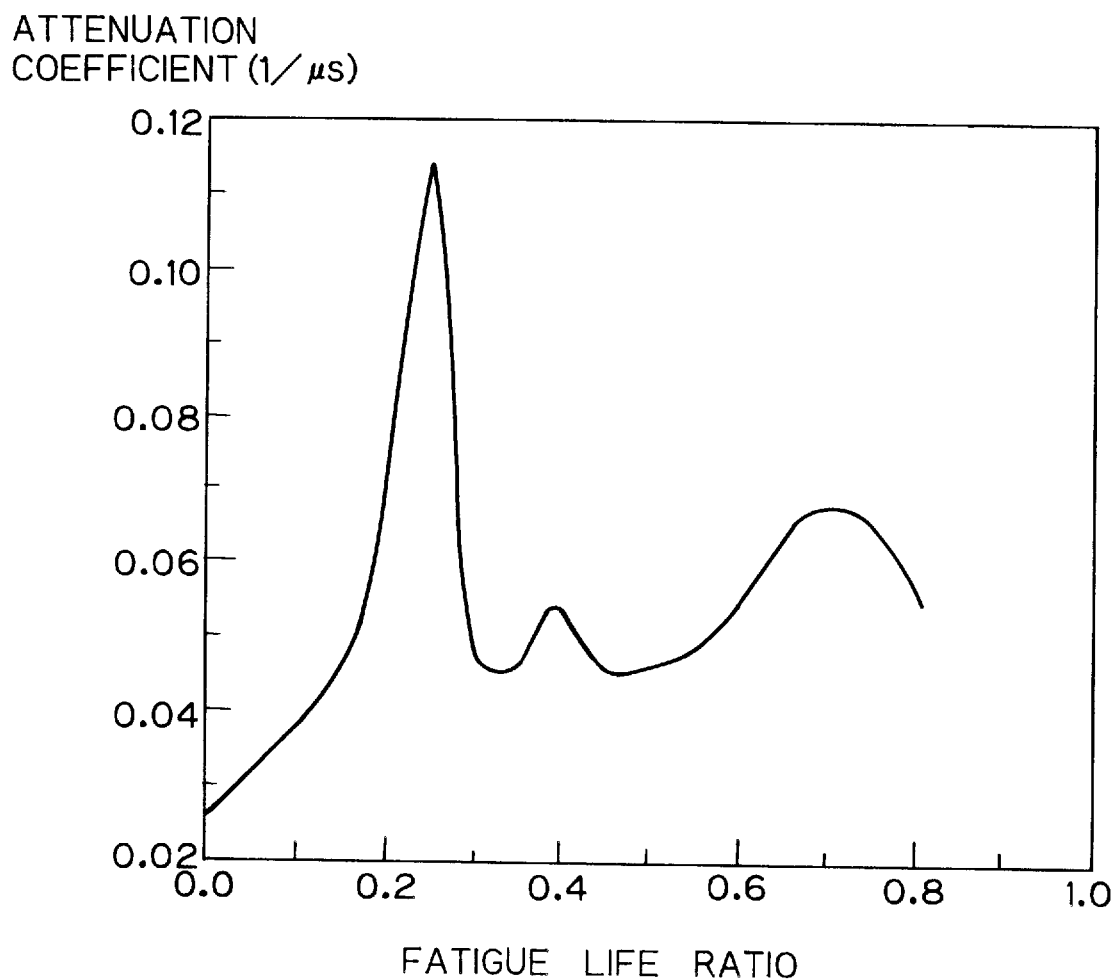
FIG. 21 is a graph illustrating the result of the relationships between an attenuation coefficient and fatigue life ratio measured by the inspection system shown in FIG. 18.

FIG. 21 illustrates the results of detection of attenuation characteristics to monitor a fatigue developing of an object, using the system shown in FIG. 18 with the electromagnetic acoustic resonance method. The material of the object was pure copper and the resonance frequency thereof was near 4 MHz. As is apparent from the graph in FIG. 21, the attenuation coefficient exhibits a peak value at approximately 25% of fatigue life. While materials extracted even from the same manufacturing lot differ in the number of fatigue cycle corresponding to the peak and the number of fatigue cycle associated with fatigue fracture, they exhibit substantially the same fatigue life ratio value (number of repetitions/number of times of fatigue rupture) corresponding to the peak value.

Figure 4A:
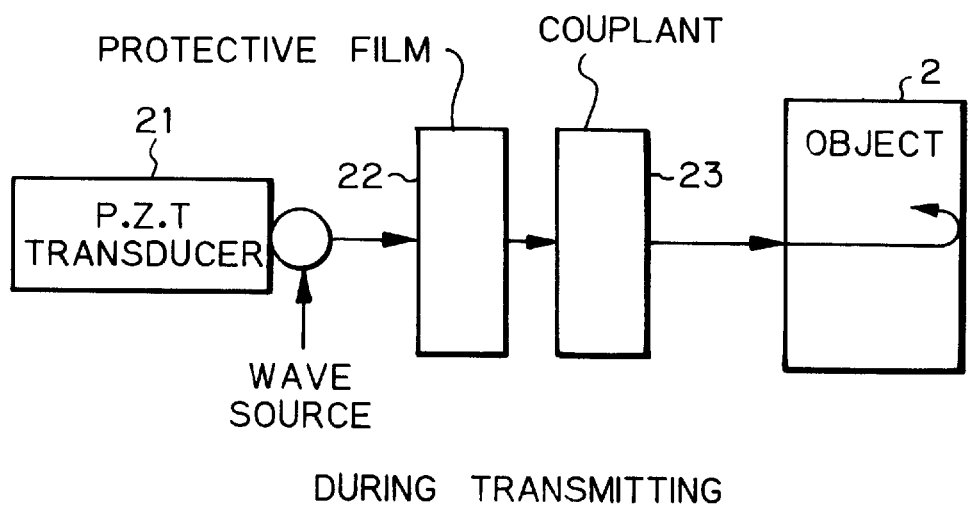
FIG. 4(a) is a diagram illustrating the propagation of ultrasonic waves from a piezoelectric vibrator to an object during transmission period.
Figure 4B:
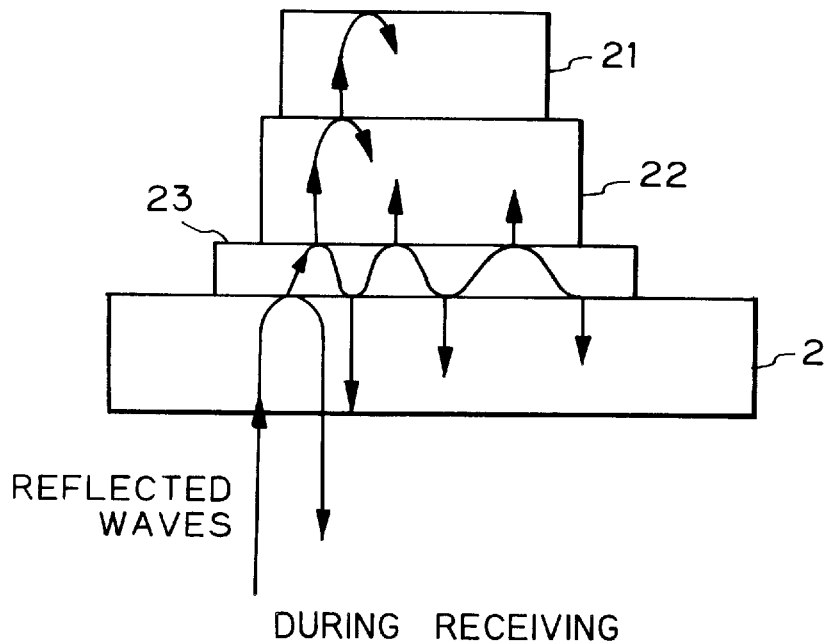
FIG. 4(b) is a diagram illustrating the propagation of ultrasonic waves between a piezoelectric ultrasonic transducer and an object contacting ultrasonic transducer, during reception period.
Figure 5:
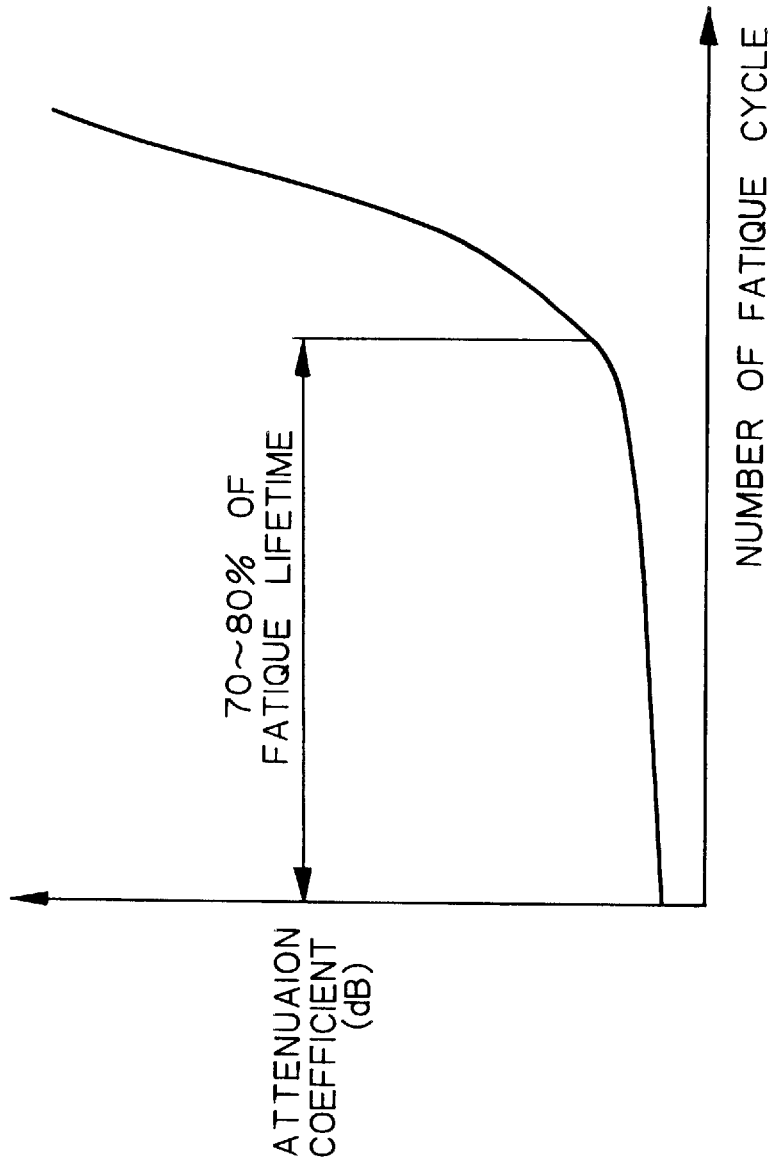
FIG. 5 is a graph illustrating a change in attenuation in a fatigue progress measured by a prior art approach.
Figure 22:
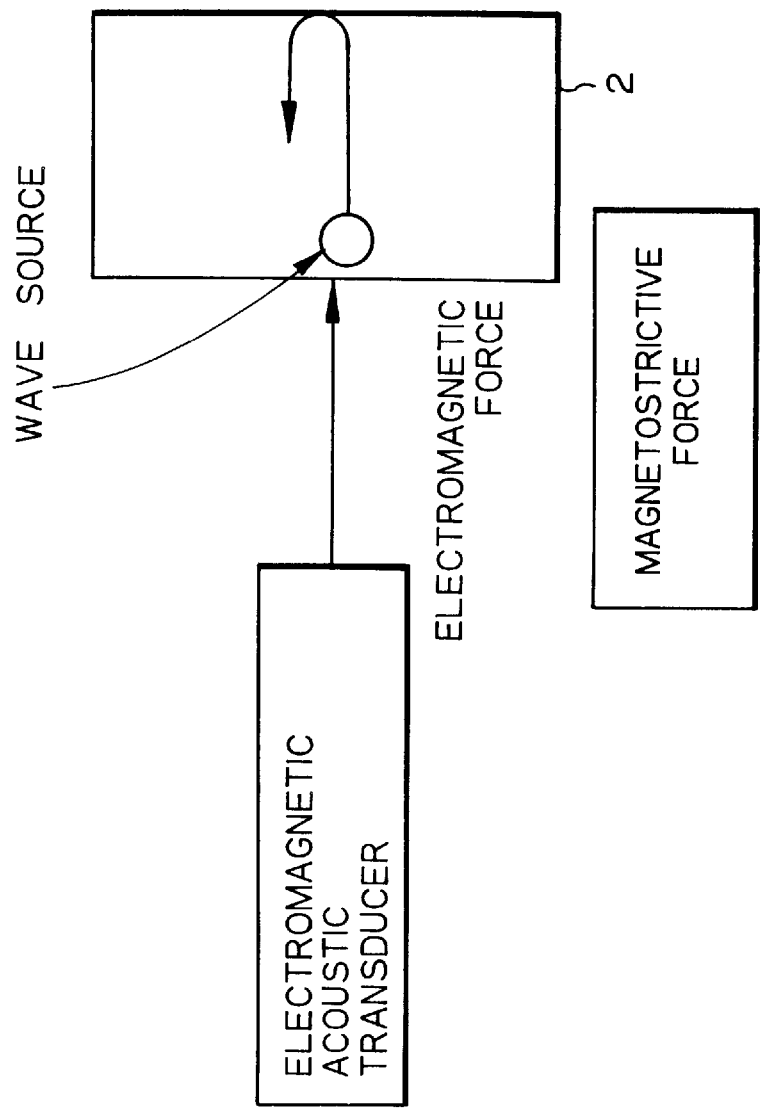
FIG. 22 is a diagram illustrating behaviors of ultrasonic waves generated by an electromagnetic acoustic transducer, according to the present invention.

By making measurements in accordance with the electromagnetic acoustic resonance method using the electromagnetic acoustic transducer (or the magnets 3a, 3b and the coil unit 6), ultrasonic waves are generated directly on the measurement surface of the object 2, as illustrated in FIG. 22, so that no interface (see the interface between the piezoelectric ultrasonic transducer 21 and the protective film 22, the interface between the protective film 22 and the acoustic couplant 23, and the interface between the acoustic couplant 23 and the object 2 in FIG. 4) exists in the propagation path of ultrasonic waves. Thus, the signal transduced from the ultrasonic waves by the electromagnetic acoustic transducer does not include disturbance. Also, the surfaces of the object 2 need not be finely finished. Further, since an absolute value of the absolute attenuation coefficient of the object 2 can be directly measured, it is possible to accurately capture changes in the object during a fatigue process.

In addition, as illustrated in FIG. 19, as fatigue advances, the attenuation coefficient begins to increase, exhibits a peak value at 20–30% of the lifetime, abruptly drops after the peak, and again increases till fracture. Since such data on change in attenuation in the fatigue progress are utilized in the database, accurate prediction of the lifetime assessment of fatigue damage can be obtained.

It is further understood by those skilled in the art that the forgoing description is preferred embodiments of the present invention and that various changes and modifications may be made in the invention without departing from the spirit and scope thereof.

What is claimed is:

1. An electromagnetic acoustic transducer comprising:
a magnet element configured to provide a static magnetic field to an object to be inspected; and
a sheet coil element having a transmitting coil of electrically conductive material supplied from a source with a burst current to cooperate with said magnet element to cause ultrasonic waves to be generated within said object, a detecting coil of electrically conductive material to detect the ultrasonic waves received from said object, and a first insulation layer between the transmitting coil and the detecting coil said coils positioned on opposite surfaces of said first insulation layer so as to be coincident with each other through said first insulation layer.

2. The electromagnetic acoustic transducer according to claim 1, wherein each of said coils is a spiral coil.

3. The electromagnetic acoustic transducer according to claim 1, wherein
said sheet coil element further comprises, a second insulation layer covering the transmitting coil and a third insulation layer covering the detecting coil, and wherein first ends and second ends of said transmitting coil and said detecting coil extend through through-holes formed through said first and second insulation layers to a surface of said electromagnetic acoustic transducer where said first ends are connected to external leads and said second ends are commonly connected to form a common ground terminal.

4. The electromagnetic acoustic transducer according to claim 2, wherein said magnet element comprises a pair of solenoid coils.

5. The electromagnetic acoustic transducer according to claim 1, wherein each of said coils is a meander coil.

6. The electromagnetic acoustic transducer according to claim 4, wherein said magnet element comprises a pair of spaced apart permanent magnets.

7. The electromagnetic acoustic transducer according to claim 5, wherein said magnet element comprises a permanent magnet having a U-shape with two leg portions and said sheet coil element is formed between the two leg portions of said permanent magnet over said object.

8. The electromagnetic acoustic transducer according to claim 5, wherein said magnet element comprises a permanent magnet.

9. The electromagnetic acoustic transducer according to claim 5, wherein said magnet element comprises a solenoid coil.

10. The electromagnetic acoustic transducer according to claim 5, wherein said sheet coil element having said meander coils has a flexibility permitting the sheet coil element to be applied along a surface of the object, said object having a cylindrical shape.

11. The electromagnetic acoustic transducer according to claim 10, wherein said magnet element comprises a solenoid coil which has an inner diameter said object having said sheet coil element applied along the surface of the object so as to be surrounded by said solenoid coil and to extend inside said solenoid coil along a longitudinal axis of said solenoid coil.

12. The electromagnetic acoustic transducer according to claim 10, wherein said magnet element further comprises a solenoid coil and a core of magnetic material which has a first portion that extends inside said solenoid coil along a longitudinal axis of said solenoid coil.

13. The electromagnetic acoustic transducer to claim 12, wherein said core has a diameter smaller than the inside diameter of the object having a cylindrical shape, and wherein another portion of said core extends inside of said object.

14. The electromagnetic acoustic transducer according to claim 12, wherein said core has a U-shape, a central portion of said U-shape core being between two leg portions and forming the first portion that extends inside said solenoid coil with the two leg portions terminating in ring portions surrounding separate parts of said object.

15. The electromagnetic acoustic transducer according to claim 14, wherein each of said ring portions is divided into at least two parts thereby to facilitate insertion of the object.

16. The electromagnetic acoustic transducer according to claim 5, wherein said magnet element comprises a pair of permanent magnets and said sheet coil element is formed as a pair of sheet coil units which are positioned between said permanent magnets.

17. The electromagnetic acoustic transducer according to claim 5, wherein said magnet element comprises a permanent magnet, and said sheet coil element is formed between said object and said permanent magnet.

* * * * *